US010575979B2

(12) United States Patent
Ghajar

(10) Patent No.: US 10,575,979 B2
(45) Date of Patent: Mar. 3, 2020

(54) SUBJECT-MOUNTED DEVICE TO MEASURE RELATIVE MOTION OF HUMAN JOINTS

(71) Applicant: Jamshid Ghajar, New York, NY (US)

(72) Inventor: Jamshid Ghajar, New York, NY (US)

( * ) Notice: Subject to any disclaimer, the term of this patent is extended or adjusted under 35 U.S.C. 154(b) by 1303 days.

(21) Appl. No.: 13/962,852

(22) Filed: Aug. 8, 2013

(65) Prior Publication Data

US 2014/0081180 A1 Mar. 20, 2014

Related U.S. Application Data

(63) Continuation-in-part of application No. 12/700,035, filed on Feb. 4, 2010, now Pat. No. 8,834,394.
(Continued)

(51) Int. Cl.
*A61F 5/055* (2006.01)
*A61F 5/058* (2006.01)
*A61B 5/11* (2006.01)

(52) U.S. Cl.
CPC ............ *A61F 5/05883* (2013.01); *A61B 5/11* (2013.01); *A61F 5/055* (2013.01)

(58) Field of Classification Search
CPC ........... A42B 3/00; A42B 3/04; A42B 3/0406; A42B 3/0473; A42B 3/06; A61B 5/00; A61B 5/0002; A61B 5/0004; A61B 5/0015; A61B 5/0024; A61B 5/0048; A61B 5/0053; A61B 5/103; A61B 5/1036; A61B 5/107; A61B 5/11; A61B 5/116; A61B 5/1126; A61B 5/48; A61B 5/486; A61B 5/68; A61B 5/6801; A61B 5/6802;
(Continued)

(56) References Cited

U.S. PATENT DOCUMENTS

| 1,136,307 A | 4/1915 | Bourdon |
| 1,301,276 A | 4/1919 | Kroetz |

(Continued)

FOREIGN PATENT DOCUMENTS

WO  WO 2007/120764 A2  10/2007

OTHER PUBLICATIONS

Amann, Laser Ranging: a critical review of usual techniques for distance measurement, Op. Eng 40(1), Jan. 10-19, 2001, pp. 10-19.
(Continued)

*Primary Examiner* — Anna K Kinsaul
*Assistant Examiner* — Camtu T Nguyen
(74) *Attorney, Agent, or Firm* — Morgan, Lewis & Bockius LLP

(57) ABSTRACT

The relational motion detection system measures relative motion of a head of a subject relative to a torso of a subject. The system includes a first motion detection sensor on a first apparatus configured to be secured to a head of a subject to detect a first motion. It also includes a second motion detection sensor on a second apparatus configured to be secured to the torso of a subject to detect a second motion. The system further includes a control unit configured to obtain information regarding the first motion from the first motion detection sensor and second motion from the second motion detection sensor, wherein the control unit contains instructions for calculating motion of the head relative to the torso of the subject based on the obtained first motion and second motion.

22 Claims, 18 Drawing Sheets

Related U.S. Application Data

(60) Provisional application No. 61/150,480, filed on Feb. 6, 2009.

(58) Field of Classification Search
CPC ... A61B 5/6803; A61B 5/6812; A61B 5/6813; A61B 5/6814; A61B 5/6822; A61B 5/6823; A61B 5/684; A61B 5/6843; A61B 5/6844; A61B 5/70; A61F 5/05883; A61F 5/055; A61F 5/05
USPC ...... 2/6.8, 44, 129, 410, 411, 413, 425, 456, 2/468; 128/97.1, 846, 857; 600/553, 600/587, 594, 595; 602/5, 12, 17–19, 602/32–35; 702/19, 33, 41–42, 108, 702/113–116, 138–139, 141, 150–151
See application file for complete search history.

(56) References Cited

U.S. PATENT DOCUMENTS

| | | |
|---|---|---|
| 1,409,326 A | 3/1922 | Williamson |
| 3,041,623 A | 7/1962 | Glahe |
| 3,134,106 A | 5/1964 | Shaffer et al. |
| 3,148,375 A | 9/1964 | Jones |
| 3,242,500 A | 3/1966 | Derr |
| 3,258,010 A | 6/1966 | Austin et al. |
| 3,471,145 A | 10/1969 | Berger |
| 3,497,872 A | 3/1970 | Mitchell |
| 3,671,974 A | 6/1972 | Sims |
| 3,818,509 A | 6/1974 | Romo et al. |
| 3,873,996 A | 4/1975 | Varteressian |
| 3,879,761 A | 4/1975 | Bothwell |
| 3,889,668 A | 6/1975 | Ochs et al. |
| 3,900,896 A | 8/1975 | Ackerman |
| 4,020,507 A | 5/1977 | Morton |
| 4,219,193 A | 8/1980 | Newman |
| 4,338,685 A | 7/1982 | LaPorta, Jr. |
| 4,489,919 A | 12/1984 | Ostrobrod |
| 4,501,023 A | 2/1985 | Bilberry |
| 4,638,510 A | 1/1987 | Hubbard |
| 4,664,341 A | 5/1987 | Cummings |
| 4,697,289 A | 10/1987 | Luigi |
| 4,825,476 A | 5/1989 | Andrews |
| 4,846,313 A | 7/1989 | Sharp |
| 4,909,459 A | 3/1990 | Patterson |
| 4,945,305 A | 7/1990 | Blood |
| 5,027,833 A | 7/1991 | Calkin |
| 5,123,408 A | 6/1992 | Gaines |
| 5,210,894 A | 5/1993 | Minton |
| 5,219,206 A | 6/1993 | Anthony et al. |
| 5,242,377 A | 9/1993 | Boughner et al. |
| 5,248,293 A | 9/1993 | Hubbard et al. |
| 5,261,125 A | 11/1993 | Cartwright et al. |
| 5,287,562 A | 2/1994 | Rush, III |
| 5,313,670 A | 5/1994 | Archer, III |
| 5,314,404 A | 5/1994 | Boughner et al. |
| 5,329,933 A | 7/1994 | Graf |
| 5,336,138 A | 8/1994 | Arjawat |
| 5,338,062 A | 8/1994 | Kiuchi et al. |
| 5,371,905 A | 12/1994 | Keim |
| 5,433,201 A | 7/1995 | Manthey |
| 5,437,613 A | 8/1995 | Reggio et al. |
| 5,517,699 A | 5/1996 | Abraham, II |
| 5,546,601 A | 8/1996 | Abeyta |
| 5,581,816 A | 12/1996 | Davis |
| 5,715,541 A | 2/1998 | Landau |
| 5,920,395 A | 7/1999 | Schulz |
| 5,930,843 A | 8/1999 | Kelly |
| 5,955,879 A | 9/1999 | Durdle et al. |
| 6,006,368 A | 12/1999 | Phillips |
| 6,009,566 A | 1/2000 | Hubbard |
| 6,052,835 A | 4/2000 | O'Shea |
| RE36,691 E | 5/2000 | Pinsen |
| 6,126,043 A | 10/2000 | Albert, II |
| 6,330,722 B1 | 12/2001 | Betts |
| 6,385,781 B1 | 5/2002 | Rose et al. |
| 6,418,564 B1 | 7/2002 | Sheridan |
| 6,481,026 B1 | 11/2002 | McIntosh |
| 6,751,809 B1 | 6/2004 | Cooper et al. |
| 6,819,354 B1 * | 11/2004 | Foster ............... H04N 7/183 348/157 |
| 6,874,170 B1 | 4/2005 | Aaron |
| 6,931,669 B2 | 8/2005 | Ashline |
| 6,968,576 B2 | 11/2005 | McNeil et al. |
| 6,971,123 B2 | 12/2005 | Weaver |
| 6,978,523 B2 | 12/2005 | Downing et al. |
| 6,984,208 B2 | 1/2006 | Zheng |
| 7,120,982 B2 | 10/2006 | Downing et al. |
| 7,155,747 B2 | 1/2007 | Baker |
| 7,165,785 B2 | 1/2007 | Bouladian |
| 7,210,240 B2 | 5/2007 | Townsend et al. |
| 7,231,698 B2 | 6/2007 | Downing et al. |
| 7,234,210 B2 | 6/2007 | Stiles et al. |
| 7,387,598 B2 | 6/2008 | Miller |
| 7,426,773 B2 | 9/2008 | Downing et al. |
| 8,181,281 B2 | 5/2012 | Nagely et al. |
| 2003/0088906 A1 | 5/2003 | Baker |
| 2004/0194194 A1 | 10/2004 | McNeil et al. |
| 2005/0067816 A1 * | 3/2005 | Buckman ............ A41D 13/018 280/730.1 |
| 2005/0177065 A1 | 8/2005 | Ghajar |
| 2007/0010772 A1 * | 1/2007 | Ryan .................. A61F 5/0123 602/26 |
| 2007/0186239 A1 | 8/2007 | Briggs |
| 2007/0186329 A1 | 8/2007 | Baker |
| 2007/0245464 A1 | 10/2007 | Baker |
| 2008/0209617 A1 | 9/2008 | Castillo |
| 2008/0313791 A1 * | 12/2008 | Nagely ............... A42B 3/0473 2/425 |
| 2009/0064396 A1 | 3/2009 | Ghajar |
| 2009/0158509 A1 | 6/2009 | Ghajar |
| 2013/0131554 A1 | 5/2013 | Dunias et al. |

OTHER PUBLICATIONS

Anonymous, A Library of Textile Sensors: Capturing Movement and Touch with Fabric, Apr. 18, 2011, 9 pgs.

Benet, Using infrared sensors for distance measurement in mobile robots, Robotics and Autonomous Systems 1006 (2002), 12 pgs.

Gallagher, An Efficient Real-Time Human Posture Tracking Algorithm Using Low-Cost Inertial and Magnetic Sensors, Proc. Int'l. Conference on Intelligent Robots and Systems, Sendai, JP, Sep. 28-Oct. 2, 2004, pp. 2967-2972.

Klotz, 24GHz Radar Sensors for Automotive Applications, Technical Univ. of Hamburg—Harburg, May 1999, pp. 359-362.

Ghajar, Communication pursuant to Article 94(3) EPC, EP 06813639.9, dated May 3, 2013, 5 pgs.

Ghajar, International Search Report and Written Opinion, PCT/US07/09028, dated Nov. 14, 2007, 8 pages.

Hans Device, en.wikipedia.org/wiki/HANS_device, Wikipedia—the free encyclopedia, downloaded Apr. 11, 2009, 5 pages.

Schalen, Quantification of tracking eye movements in normal subjects, Acta Oto-Laryngologica Nov.-Dec. 1980, vol. 90, No. 5-6, Nov. 1980, pp. 404-413.

* cited by examiner

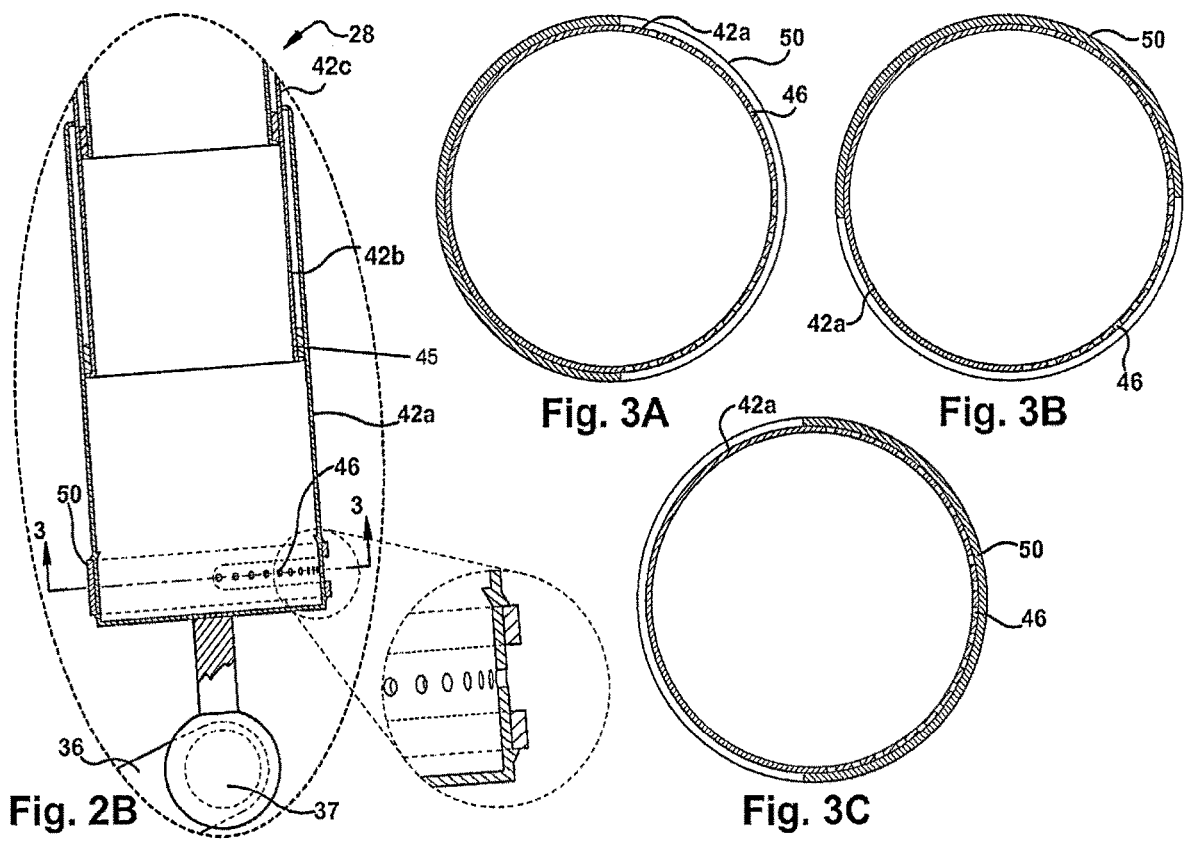

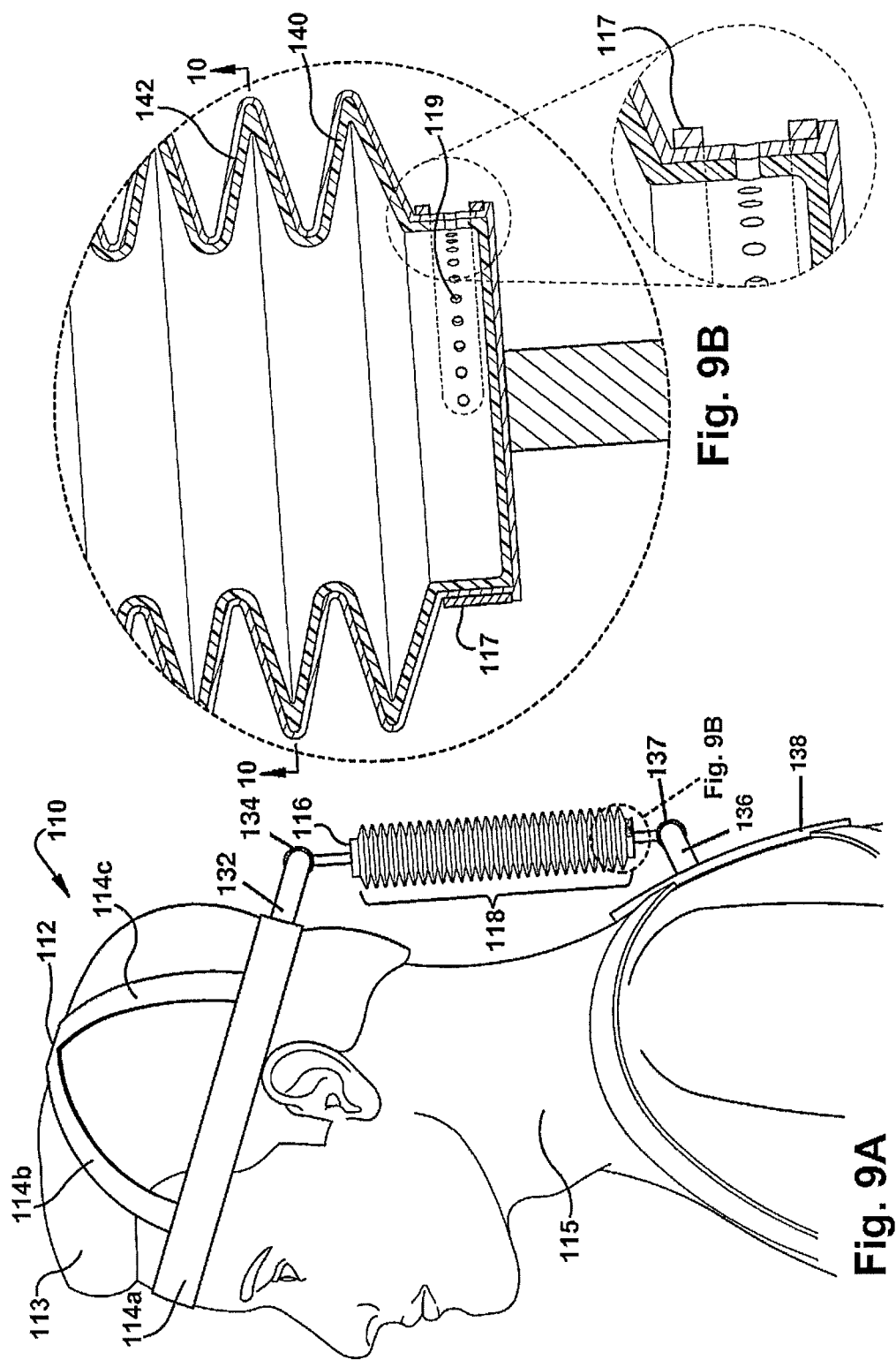

SUBJECT-MOUNTED DEVICE TO MEASURE RELATIVE MOTION OF HUMAN JOINTS

RELATED APPLICATION

This application is a continuation-in-part of and claims the benefit of and priority to U.S. patent application Ser. No. 12/700,035, filed Feb. 4, 2010, which claims benefit and priority to U.S. Provisional Application Ser. No. 61/150,480, filed Feb. 6, 2009, the entirety of these two applications are hereby incorporated herein by reference.

TECHNICAL FIELD

The present disclosure relates to devices for reducing brain and cervical spine injury, and more particularly to devices and methods for preventing the head from substantial rotational acceleration or deceleration that could lead to tearing of brain or cervical spine tissue.

BACKGROUND

Rapid acceleration and deceleration of a person's head, especially with a rotational component, can cause shearing damage to the white matter that connects neurons in the brain, resulting in concussion symptoms, and even coma, when the shearing is severe. Disruption of white matter connections disables brain function. Symptoms can be as mild as memory and attention difficulties, and as serious as a coma state. This is the most common form of brain injury and has been shown to occur in car crashes, falls, sporting accidents and combat as a consequence of road-side bombs that cause a blast wave to whip the head producing rotational shear injury. In addition, high acceleration and rapid deceleration in flexion, extension or rotation movements can cause cervical spine fractures, torn ligaments, disc herniations, spinal cord injury and other damage of the neck. Rapid rotation and whiplash of the head is exaggerated by the flexibility of the neck, which is unable to effectively resist sudden loads, whether the load is from an impact, rapid deceleration or a blast wave. These sudden skull rotations can induce the brain to move inside the skull, stretching or tearing tissue within the white matter of the brain through inertial effects.

SUMMARY

Devices and methods for reducing brain and cervical spine injury are disclosed herein.

According to the aspects illustrated herein, there is provided a device that includes a headpiece sufficiently designed to secure to a user's head, the headpiece having a first attachment member; a support harness sufficiently designed to secure to the user's torso, the support harness having a second attachment member; and a telescoping member having a main tube and a series of progressively smaller diameter tubes nested within each other, wherein the smaller diameter tubes are adapted to extend and compress in a linear plane by the intake and outflow of fluid, wherein the telescoping member has a first engaging member for engaging the first attachment member, and wherein the telescoping member has a second engaging member for engaging the second attachment member, wherein the first engaging member and the first attachment member form a ball and socket joint adapted to allow three degrees of freedom, permitting rotary movement in all directions through the movement of the first engaging member in the first attachment member, and wherein the second engaging member and the second attachment member form a ball and socket joint adapted to allow three degrees of freedom, permitting rotary movement in all directions through the movement of the second engaging member in the second attachment member. In an embodiment, the first engaging member of the telescoping member connects with the first attachment member of the headpiece approximately at a level of the user's inion. In an embodiment, the second engaging member of the telescoping member connects with the second attachment member of the support harness approximately at a level of the user's C7/T1 spinous processes.

According to the aspects illustrated herein, there is provided a device that includes a headpiece sufficiently designed to secure to a user's head, the headpiece having a first attachment member; a support harness sufficiently designed to secure to the user's torso, the support harness having a second attachment member; and a telescoping member having expansion bellows adapted to extend and compress in a linear plane by the intake and outflow of fluid, wherein the telescoping member has a first engaging member for engaging the first attachment member, and wherein the telescoping member has a second engaging member for engaging the second attachment member, wherein the first engaging member and the first attachment member form a ball and socket joint adapted to allow three degrees of freedom, permitting rotary movement in all directions through the movement of the first engaging member in the first attachment member, and wherein the second engaging member and the second attachment member form a ball and socket joint adapted to allow three degrees of freedom, permitting rotary movement in all directions through the movement of the second engaging member in the second attachment member. In an embodiment, the first engaging member of the telescoping member connects with the first attachment member of the headpiece approximately at a level of the user's inion. In an embodiment, the second engaging member of the telescoping member connects with the second attachment member of the support harness approximately at a level of the user's C7/T1 spinous processes.

According to aspects illustrated herein, there is provided a method for preventing brain and cervical spine injury that includes providing a device comprising a headpiece sufficiently designed to secure to the user's head, the headpiece having a first attachment member; a support harness sufficiently designed to secure to the user's torso, the support harness having a second attachment member; an acceleration threshold device sufficiently designed to detect external forces experienced by the user's head and for providing an output signal to a processor circuit; and a telescoping member adapted to extend and compress in a linear plane by the intake and outflow of fluid, wherein the telescoping member has a first engaging member for engaging the first attachment member, the first engaging member and the first attachment member forming a ball and socket joint adapted to allow three degrees of freedom, permitting rotary movement in all directions through the movement of the first engaging member in the first attachment member, and wherein the telescoping member has a second engaging member for engaging the second attachment member, the second engaging member and the second attachment member forming a ball and socket joint adapted to allow three degrees of freedom, permitting rotary movement in all directions through the movement of the second engaging member in the second attachment member; connecting the first engaging member of the telescoping member with the first attachment member of the headpiece approximately at a level of the user's inion; connecting the second engaging member of the telescoping member with the second attachment member of the support harness approximately at a level of the user's C7/T1 spinous processes; detecting, using an acceleration threshold detector, external contact forces experienced by the user's head to determine acceleration of the user's head; providing, using the acceleration threshold detector, an output signal representing if the determined acceleration experienced by the user's head reached a predetermined threshold; receiving, using a processor, the output signal from the acceleration threshold detector; and generating, using the processor, an event signal to trigger the intake or outflow of fluid by the telescoping member in response to the determined acceleration.

According to some embodiments, there is provided a relational motion detection system for measuring relative motion of a head of a subject relative to a torso of the subject. The system includes a first motion detection sensor on a first apparatus configured to be secured to a head of a subject to detect a first motion. The system also includes a second motion detection sensor on a second apparatus configured to be secured to the torso of the subject to detect a second motion. The system further includes a control unit configured to obtain information related to the first motion from the first motion detection sensor and information related to the second motion from the second motion detection sensor. The control unit contains instructions for calculating motion of the head relative to the torso of the subject based on the obtained information related to the first motion and second motion.

Similarly, according to some embodiments, a subject mounted relational motion detection system measures relative motion of a head of a subject relative to a torso of the subject. The a subject mounted relational motion detection system detects a first motion using a first motion detection sensor mounted to the head of the subject, and detects a second motion with a second motion detection sensor mounted to the torso of the subject. Then, the motion of the head relative to the torso of the subject is calculated based on the detected first motion and second motion. In some embodiments, when the calculated motion exceeds a threshold motion of the subject's head relative to the torso of the subject, the motion is dampened using one or more of the mechanisms and methods described in the detailed description below.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 2B shows an exploded view of the telescoping member of FIG. 2A. The telescoping member includes perforated portions allowing entry and exit of fluid into and out of the telescoping member and an outer rotatable circular member for controlling the entry and exit of fluid through the perforated portions. The inset shows a close-up view of the relationship between the perforated portions of the telescoping member and the outer circular member.

FIG. 3A, FIG. 3B and FIG. 3C show cross-sectional views of the telescoping member of FIG. 2B taken along line 3-3. FIG. 3A shows the outer circular member in a fully open position, allowing complete fluid flow into and out of the telescoping member. FIG. 3B shows the outer circular member in a partially open position, allowing partial fluid flow into and out of the telescoping member. FIG. 3C shows the outer circular member in a closed position, inhibiting fluid flow into and out of the telescoping member.

FIG. 9A shows a side view of an embodiment of a device of the present disclosure in a neutral position on a user. The device includes a headpiece, a support harness and a telescoping member having expansion bellows.

FIG. 9B shows an exploded view of the telescoping member of FIG. 9A. The inset shows a close-up view of the relationship between the perforated portions of the telescoping member and the outer circular member. The telescoping member includes perforated portions allowing entry and exit of fluid into and out of the telescoping member and an outer circular member for controlling the entry and exit of fluid through the perforated portions.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Devices and methods for reducing brain and cervical spine injury are disclosed herein. The devices disclosed herein can be used to protect the brain, the cervical spine, and/or the spinal cord from high accelerations and rapid decelerations of the head in all axes. In an embodiment, a device of the present disclosure is a neck bracing system that allows normal motion of the head, but dampens head movement in response to rapid acceleration or decelerations at a threshold that would produce brain injury, cervical spine, or spinal cord injury.

Figure 1:
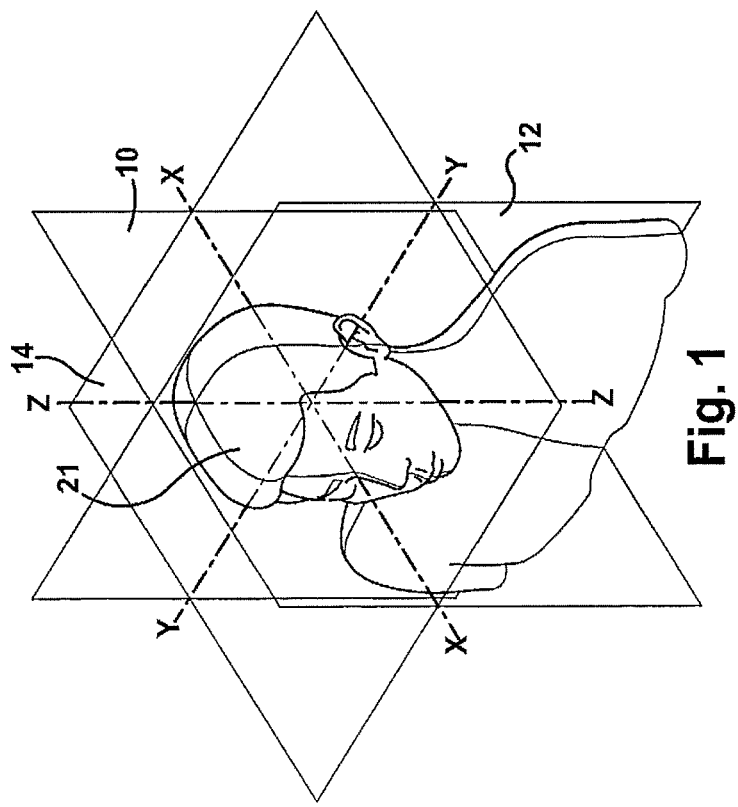
FIG. 1 shows a front view of the three rotational planes, coronal (Y), axial (X) and sagittal (Z) planes or axes, through a person's head.

FIG. 1 shows the three planes in which a person's head 21 can rotate. The coronal plane 12 lies roughly parallel to the chest. Moving the head 21 side to side, or moving the ear toward the shoulder, is an example of head rotation in the coronal plane 12. The axial plane 14 perpendicular to coronal plane 12 lies roughly parallel to the top of the head 21, like the rim of a hat. Shaking one's head to indicate "no, is an example of rotation in the axial plane 14. The sagittal plane 10 is perpendicular to both planes 12 and 14, and bisects the left side of the head 21 from the right. Nodding one's head to indicate, "Yes," is an example of rotation in the sagittal plane 10.

Figure 2A:
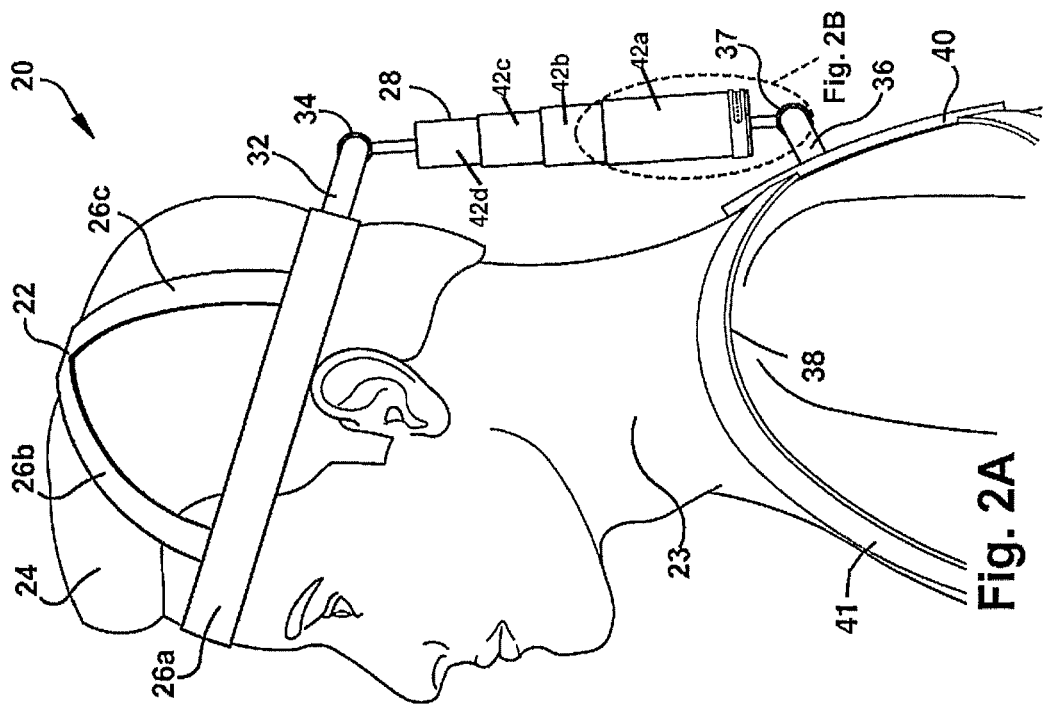
FIG. 2A shows a side view of an embodiment of a device of the present disclosure in a neutral position on a user. The device includes a headpiece, a support harness and a telescoping member having a main tube and a series of progressively smaller diameter tubes nested within each other.

An embodiment of a device 20 of the present disclosure for reducing brain and cervical spine injury is shown in the various illustrations of FIGS. 2A-8. As illustrated in FIG. 2A, the device 20 includes a headpiece 22 for securing to a person's head 24. In the embodiment depicted in FIG. 2A, the headpiece 22 is a head harness composed of interconnected straps 26a, 26b and 26c. The straps 26a, 26b and 26c can be made out of leather, plastic, cloth, rubber and any other material as the present disclosure is not intended to be limited in this manner. As illustrated in FIG. 2A, one strap 26a is positioned circumferentially about the head 24, and two straps 26b and 26c, are positioned in a criss-cross manner on top of the head 24. In an embodiment, there may be more or less straps for securing to the head 24 as the present disclosure is not intended to be limited in this manner. The straps 26a, 26b and 26c can be positioned in different arrangements on or around the head 24 and still be within the scope of the presently disclosed embodiments. The straps 26a, 26b and 26c can be fabricated from one single material or out of multiple pieces of material that are engaged together. The headpiece 22 includes a first attachment member 32 located at a rear of the strap 26a. In an embodiment, the first attachment member 32 attaches to the strap 26a at the back of the head 24 at approximately the level of the inion.

Although the embodiments depicted in FIGS. 2A-8 show the headpiece 22 as a head harness, other headpieces can be used with the device 20. In an embodiment, a headpiece for use with the device 20 is a helmet having the appearance of a conventional football helmet. The helmet may be made out of plastic, rubber, wood or any other material as the present disclosure is not intended to be limited in this manner. In an embodiment, the helmet may not include facial protection or straps for securing the helmet to the head 24. In an embodiment, the headpiece 22, designed as a head harness, a helmet or any other similar type device, is sufficiently designed to only secure to a user's head and does not need to be secured to any other components such as, for example, components of a moving vehicle or sports training gear, to produce the desired protection.

As further shown in FIG. 2A and FIG. 2B, the device 20 includes a telescoping member 28 comprising a series of four tubes 42a, 42b, 42c and 42d of progressively smaller diameters nested within each other. It should be understood that although four segments are shown in the various figures, the telescoping member 28 may include any suitable number of tubes. In an embodiment, the telescoping member 28 is a piston-like telescoping member. The largest diameter sleeve 42a is called the main or barrel, and the smaller inner sleeves 42b, 42c and 42d are called the stages or cylindrical tubular sliding members, each stage having a successively smaller diameter than the preceding stage. The smallest stage 42d is also known as the plunger. When the telescoping member 28 is in the retracted position, the stages 42b, 42c and 42d are nested within one another in the barrel 42a. As the telescoping member 28 is extended, each nested stage 42b, 42c and 42d emerges from its neighbor and extends to its full length. In an embodiment, the telescoping member 28 defines a variable volume chamber, where the chamber has a minimum volume when the stages 42b, 42c and 42d are nested within one another, and the chamber has a maximum volume when the stages 42b, 42c and 42d are extended. The stages 42b, 42c and 42d of the telescoping member 28 may extend and compress freely during voluntary head movements and may extend and compress at reduced rates during high accelerations and rapid decelerations. The telescoping member 28 may be made out of plastic, steel, metal or any other light weight material to minimize bending of the member and allow for easy carrying.

The telescoping member 28 is sufficiently designed for extension and compression in a linear plane, and includes a first engaging member or connector 34 for engaging the first attachment member 32 of the headpiece 22, and a second engaging member or connector 37 for engaging a second attachment member 36 of a support harness 38. In an embodiment, the connector 34 is a universal joint, allowing free movement in at least 180 degrees so that the telescoping member 28 remains linear. In an embodiment, the connector 34 and the first attachment member 32 attach to the strap 26a at the back of the head 24 at approximately the level of the inion. The inion represents the middle of the back of the head 24 and additionally is located equidistantly from bottom of skull to top. The connector 34 may be detachable or removable from the first attachment member 32. The connector 34 may be fabricated from a joint, a hinge, a socket or any other device for coupling the headpiece 22 to the telescoping member 28 and allowing movement in more than one plane. In an embodiment, the connector 34 and the first attachment member 32 form a ball and socket joint allowing three degrees of freedom, permitting rotary movement of the head 24 in all directions through the movement of the connector 34 in the first attachment member 32. In such embodiments, the connector 34 terminates in a ball, and the first attachment member 32 terminates in a spherical shell sized to snugly envelope the ball of the connector 34. When the ball of the connector 34 is within the socket of the first attachment member 32, the centers of the ball and socket are coincident, resulting in a spherical geometry that facilitates full three dimensional rotation of the connector 34 and the first attachment member 32 about the coincident centers, providing multi-axial and multi-directional positioning of the head 24. In an embodiment, this full three dimensional rotation allows the head 24 to move in any direction in coronal, sagittal and axial planes, producing no bending force on the telescoping member 28, allowing the telescoping member 28 to function only in compression and extension. In an embodiment, the ball and socket joint allows free movement of the telescoping member 28 such that the telescoping member 28 remains in straight alignment and does not bend. In an embodiment, the connector 34 is made from a pliable material.

In an embodiment, the support harness 38 includes a vest or plate portion 40 and straps 41 sufficiently designed to secure to the user's torso. In an embodiment, the support harness 38 may include a chest vest. In an embodiment, the support harness 38, designed as a vest with straps, a chest vest or any other similar type device, is sufficiently designed to only secure to a user's torso and does not need to be secured to any other components such as, for example, components of a moving vehicle or sports training gear, to produce the desired protection. In an embodiment, the connector 37 attaches to the plate portion 40 of the support harness 38 at the level of the C7/T1 spinous processes. The C7/T1 spinous processes represents the top or the torso and the base of the neck 23. The connector 37 may be detachable or removable from the second attachment member 36. The connector 37 may be fabricated from a joint, a hinge, a socket or any other device for coupling the support harness 38 to the telescoping member 28 and allowing movement in more than one plane. In an embodiment, the connector 37 and the second attachment member 36 form a ball and socket joint allowing three degrees of freedom, permitting rotary movement of the head 24 in all directions through the movement of the connector 37 in the second attachment member 36. In such embodiments, the connector 37 terminates in a ball, and the second attachment member 36 terminates in a spherical shell sized to snugly envelope the ball of the connector 37. When the ball of the connector 37 is within the socket of the second attachment member 36, the centers of the ball and socket are coincident, resulting in a spherical geometry that facilitates full three dimensional rotation of the connector 37 and the second attachment member 36 about the coincident centers, providing multi-axial and multi-directional positioning of the head 24. In an embodiment, this full three dimensional rotation allows the head 24 to move in any direction in coronal, sagittal and axial planes, producing no bending force on the telescoping member 28, allowing the telescoping member 28 to function only in compression and extension. In an embodiment, the ball and socket joint allows free movement of the telescoping member 28 such that the telescoping member 28 remains in straight alignment and does not bend. In an embodiment, the connector 37 is made from a pliable material. In an embodiment, a support harness 38 is not included as part of the device 20. In such embodiments, the connector 37 can attach to a second attachment member on an external component, such as, for example, a second attachment member of a car seat in a vehicle that the user is in. In such embodiments, the connector 37 and the second attachment member form a ball and socket joint allowing three degrees of freedom, permitting rotary movement in all directions through the movement of the connector 27 in the second attachment member.

The telescoping member 28 may compress the distance between the inion and first thoracic spinous process when the head 24 and neck 23 are fully extended, which is approximately two inches, and may extend the distance, about 8 inches, between the inion and first thoracic spinous process when the head 24 and neck 23 are fully in flexion, which is approximately eight inches. The telescoping member 28 remains linear during extension and compression. In an embodiment, the telescoping member 28 includes a gas spring piston damper, a lockable gas spring piston damper with a locking device, a dynamic gas spring piston damper with a damping device or any other type of piston damper as the present disclosure is not intended to be limited in this manner.

FIG. 2B shows an exploded view of the telescoping member 28 showing sliding members 42a, 42b and 42c. In an embodiment, the telescoping member 28 extends and compresses by the intake/outflow of fluid through the telescoping member 28. In an embodiment, the fluid powering the telescoping member 28 is a gas. In an embodiment, the gas is air. In an embodiment, the fluid powering the telescoping member 28 is a liquid. In an embodiment, the liquid is a hydraulic liquid. In embodiments where the fluid powering the telescoping member 28 is a liquid, the telescoping member 28 may further comprise an airtight flexible membrane adapted to house liquid under pressure. The flexible membrane covers the inside surface of the stages and constitutes a completely sealed chamber having the liquid material therein under pressure. In embodiments where the telescoping member 28 is powered by a liquid, a container or bag may be provided and is adapted to house the liquid when the liquid is not within the flexible membrane of the telescoping member 28. The container or bag housing the liquid can be in fluid communication with the perforated portions 46 of the telescoping member 28.

The rate of fluid exchange into and out of the telescoping member 28 can be controlled using a number of voluntary or programmed cues. Perforated portions 46 of the telescoping member 28 allow entrance and exit of fluid during extension and compression of the telescoping member 28. In an embodiment, the telescoping member 28 includes gaskets 45 positioned above the perforated portions 46 that keep the telescoping member 28 airtight and to prevent fluid from entering between the sliding members 42b, 42c and 42d. The perforated portions 46 may be variably exposed by an overriding rotatable circular member 50 surrounding an outer diameter of the main tube 42a of the telescoping member 28. The outer circular member 50 can expose more or less of the perforated portions 46 as needed at the base of the telescoping member 28. In an embodiment, the outer circular member 50 can be controlled manually by turning the outer circular member 50 and exposing more or less of the perforated portions 46. In an embodiment, the outer circular member 50 can be controlled electronically. The inset shown in FIG. 2B shows a close-up view of the relationship between the perforated portions 46 of the telescoping member 28 and the outer circular member 50. In an embodiment, the outer circular member 50 may be in an entirely open position as shown in FIG. 3A where fluid may completely enter and exit the perforated portions 46, or may be in a partially open position as shown in FIG. 3B where fluid may enter and exit the perforated portions 46 at a reduced rate, or may be in an entirely closed position as shown in FIG. 3C where no fluid may enter or exit the perforated portions 46.

In an embodiment, the outer circular member 50 is controlled electronically to expose more or less of the perforated portions 46. In such embodiments, the outer circular member 50 can be controlled by an acceleration sensor arrangement comprising an acceleration threshold detector for detecting external forces experienced by the user's head to determine acceleration of the user's head and for providing an output signal; and a processor for receiving the output signal and generating an event signal to trigger the intake or outflow of fluid by the telescoping member 28 by moving the outer circular member 50 to expose more or less of the perforated portions 46.

In an embodiment, the acceleration threshold detector provides an output signal having a first value when the acceleration is less than a predetermined threshold and is arranged to switch the output signal from the first value to a second value when the acceleration reaches the predetermined threshold. The processor generates an event signal to trigger movement of the outer circular member 50 to expose more or less of the perforated portions 46, in response to the output signal from the acceleration threshold detector switching to the second value. In an embodiment, the acceleration threshold detector comprises at least one of a piezo element and a micromachined element. In an embodiment, the acceleration threshold detector is a Piezoresisitive 3-Axis acceleration sensor adapted to trigger an event (such as the intake or outflow or air by the telescoping member) when all outputs from X, Y or Z go below a predetermined set threshold. In an embodiment, the acceleration threshold detector is a MEMS accelerometer. A programmable sequence can control the movement of the outer circular member 50 to expose more or less of the perforated portions 46 such that at the predetermined threshold of acceleration there is a shut off of the fluid portal followed by a rapid release and then closure, repeating hundreds of times per second causing an oscillatory slowing of the acceleration to a full stop. If the head movement exceeds the set threshold then there is a rapid deceleration to return the movement to below threshold acceleration. Once set at a threshold, an accelerometer can activate the locking device in a lockable gas spring piston damper or the damping device in a dynamic gas spring piston damper. In an embodiment, the accelerometer may be set at a threshold of about 20 g or less or 3000 rads/second squared or less. Setting the accelerometer at this threshold may aid in preventing or ameliorating the chances of sustaining a concussion. In an embodiment, a pressure sensor integrator (rate of pressure increase and decrease) or air velocity measurement may be used in conjunction with the telescoping member 28 to set various thresholds to activate the locking device in a lockable gas spring piston damper or the damping device in a dynamic gas spring piston damper. In an embodiment, the device 20 may include an acceleration threshold detector with a set acceleration threshold and an electronic shut-off valve. In an embodiment, the acceleration threshold detector may be located on the front at a point between the eyes and mid forehead to detect acceleration in the coronal, sagittal and axial planes. When located vertically on the front, the acceleration threshold detector may detect acceleration on the sagittal plane. When located horizontally on the front, the acceleration threshold detector may detect acceleration on the axial plane. In an embodiment, the acceleration threshold detector may be located vertically at a point above the ear. This location may allow acceleration to be detected in the coronal plane.

Figure 5:
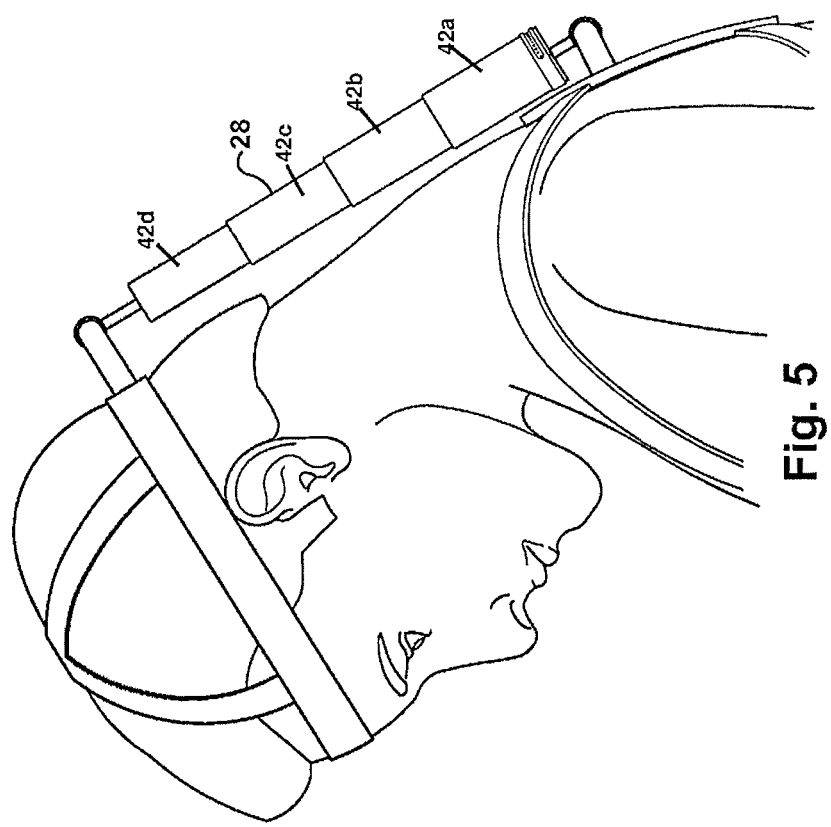
FIG. 5 shows a side view of the device of FIG. 2A on the user. The telescoping member is in a fully extended state.
Figure 4:
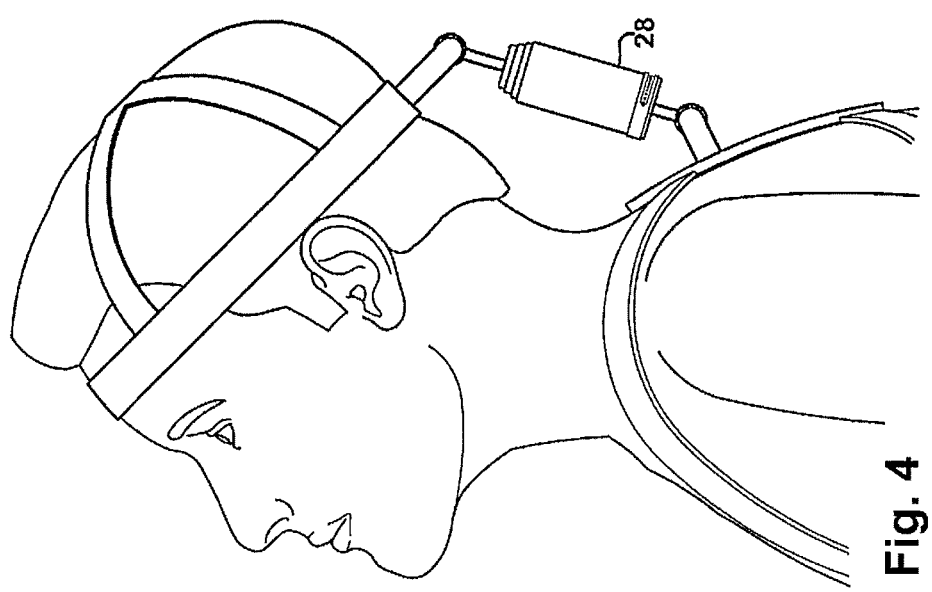
FIG. 4 shows a side view of the device of FIG. 2A on the user. The telescoping member is in a fully compressed state.
Figure 6:
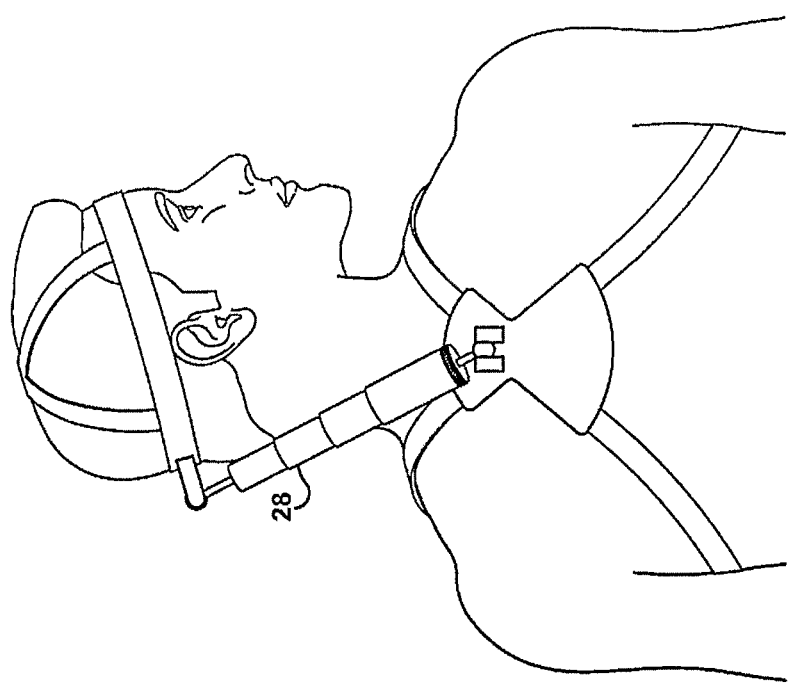
FIG. 6 shows a rear view of the device of FIG. 2A on the user. The telescoping member is in a neutral position.
Figure 7:
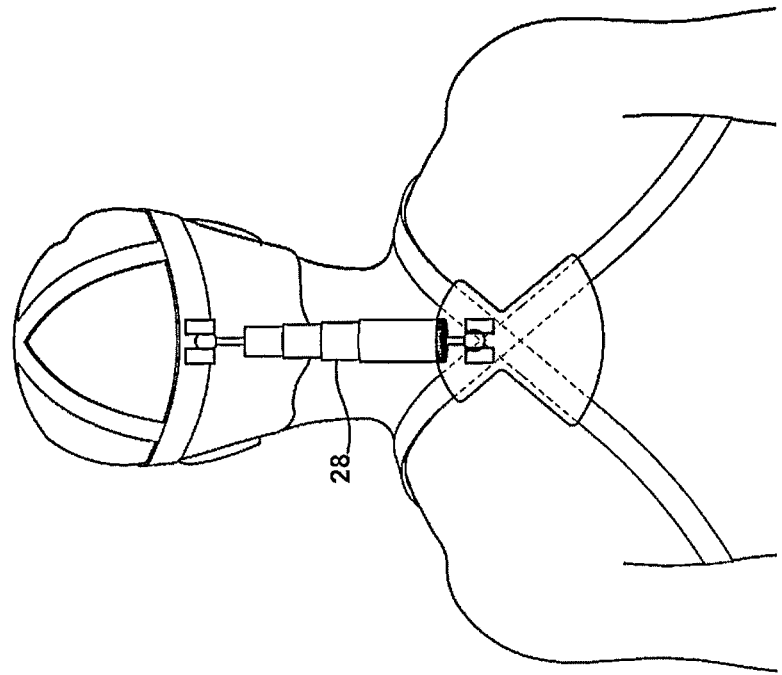
FIG. 7 shows a rear view of the device of FIG. 2A on the user. The telescoping member is in an extended position as the user's head is turned in the axial plane.
Figure 8:
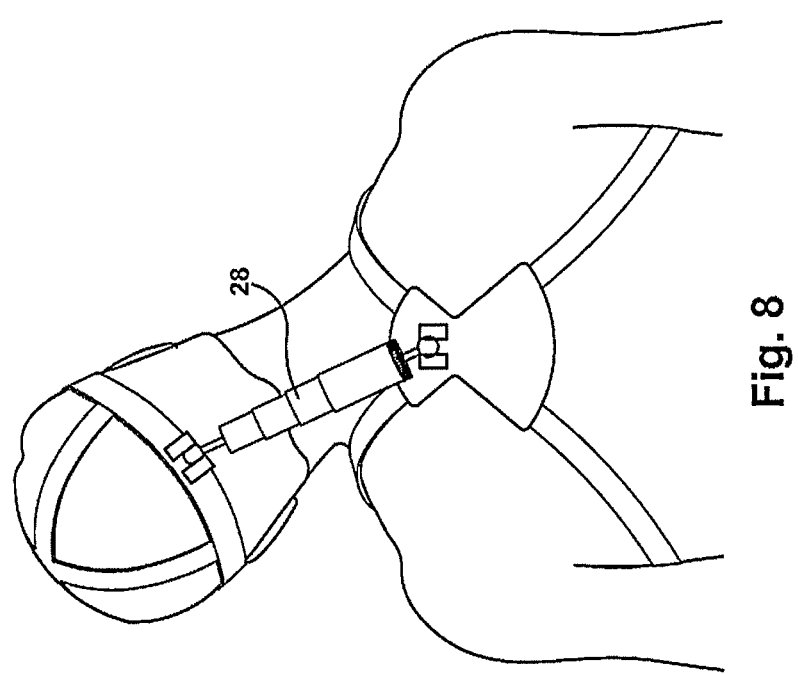
FIG. 8 shows a rear view of the device of FIG. 2A on the user. The telescoping member is in an extended position as the user's head is turned in the coronal plane.

FIGS. 4-8 show the device 20 of FIG. 2A during various head movements. The device 20 provides unencumbered head motion and range during normal circumstances. The sliding members 42b, 42c and 42d are of substantially the same length, so that they can be moved from an outstretched position, such as shown in FIG. 5, to a substantially fully telescoped or compressed position, such as shown in FIG. 4. FIG. 4 shows the telescoping member 28 fully compressed with the head 24 and the neck 23 in a fully extended position. In the outstretched position, the inner ends of the sliding members are adjacent one another. FIG. 5 shows the head 24 and the neck 23 in full flexion with the telescoping member 28 in full flexion. In the telescoped position, the inner ends of the sliding members are adjacent the outer ends of the other tube. FIG. 6 shows a rear view of the telescoping member 28 in a neutral position attached to the strap 26a at the back of the head 24 at approximately the level of the inion and attached to the support harness 38 at the level of the C7/T1 spinous processes. FIG. 7 shows the telescoping member 28 extended as the head 24 is turned in the axial plane. FIG. 8 shows the telescoping member 28 extended as the head 24 is bent in the coronal plane so the ear approaches the shoulder.

An embodiment of a device 110 of the present disclosure for reducing brain and cervical spine injury is shown in FIG. 9A. The device 110 includes a headpiece 112 for securing to a person's head 113. The headpiece 112 may be a harness or a conventional helmet such as is described in FIG. 2A. In an embodiment, the headpiece 112 may be a head harness composed of interconnected straps 114a, 114b, and 114c, like those shown in FIG. 2A. As shown in FIG. 9A, there may be one strap 114a, positioned circumferentially about the head, and two straps 114b and 114c, positioned in a criss-cross manner on top of the head 113. In an embodiment, the headpiece 112, designed as a head harness, a helmet or any other similar type device, is sufficiently designed to only secure to a user's head and does not need to be secured to any other components such as, for example, components of a moving vehicle or training gear, to produce the desired protection. The device 110 includes an accordion-like telescoping member 116 having expansion bellows 118 with convolutions that control the air which makes the accordion-like telescoping member 116 extend and compress. The bellows 118 allow for compression and expansion and little bending. In an embodiment, the bellows 118 are made from materials that allow the accordion-like telescoping member 116 to compress without bending. Examples of materials suitable for construction of the bellows 118 include, but are not limited to, plastics, steels, alloys or any other light weight materials that do not bend easily. Examples of materials suitable for the bellows 118 include, but are not limited to, stainless steel, alloys such as Inconel, Monel, Titanium and 316 stainless steel. The bellows 118 may be circular, triangular, square-shaped or any other shape as the present disclosure is not intended to be limited in this manner.

Figure 10:
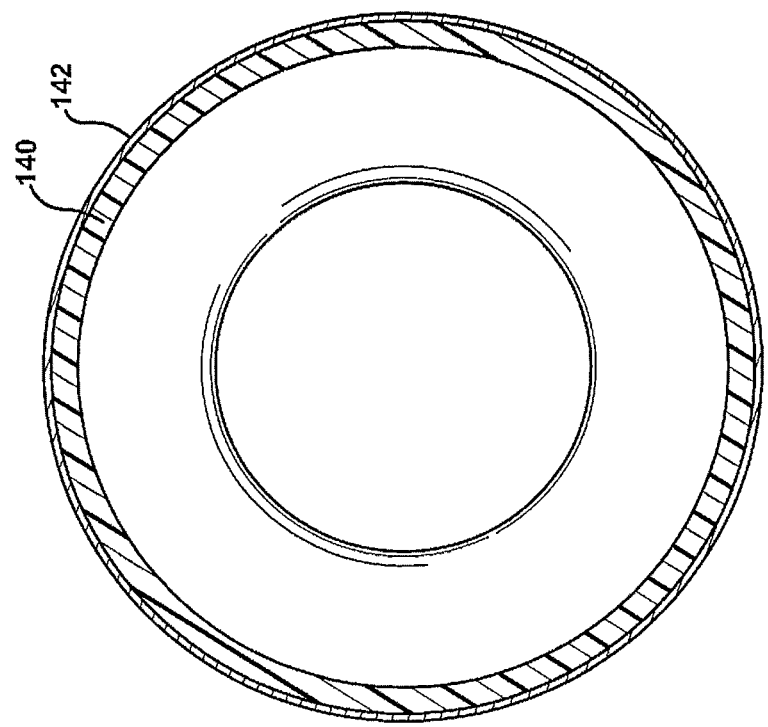
FIG. 10 shows a cross-sectional view of the telescoping member of FIG. 9B taken along line 10-10.

FIG. 9B in conjunction with FIG. 10 show close-up cut-away views of the accordion-like telescoping member 116. In an embodiment, the bellows 118 are formed from at least one inner layer 140 and at least one outer layer 142. In an embodiment, the layers 140 and 142 are airtight. The inner layer 140 may be fabricated from a material that is gas-tight and pliable, such as Gortex, polyethylene or any other similar material. The outer layer 142 may be made out of plastic, steel, metal or any other material as the present disclosure is not intended to be limited in this manner. The chamber forming the bellows 118 of the accordion-like telescoping member 116 may be filled with air, liquid, solid, gas or any other substance.

Perforated portions 119 of the accordion-like telescoping member 116 allow entrance and exit (intake/outflow) of fluid during extension and compression of the accordion-like telescoping member 116 into the airtight chamber. In an embodiment, the fluid powering the telescoping member 116 is a gas. In an embodiment, the gas is air. In an embodiment, the fluid powering the telescoping member 116 is a liquid.

In an embodiment, the liquid is a hydraulic liquid. The perforated portions 119 may be variably exposed by an overriding outer circular member 117. The outer circular member 117 can expose more or less of the perforated portions 119 as needed at the base of the accordion-like telescoping member 116. In an embodiment, the outer circular member 117 can be controlled manually by turning the outer circular member 117 and exposing more or less of the perforated portions 119. In an embodiment, the outer circular member 50 can be controlled electronically. In an embodiment, the outer circular member 117 may be completely closed where no air may enter or exit or may be entirely open where air may enter and exit.

In an embodiment, the outer circular member 117 is controlled electronically to expose more or less of the perforated portions 119. In such embodiments, the outer circular member 117 can be controlled by an acceleration sensor arrangement comprising an acceleration threshold detector for detecting external forces experienced by the user's head to determine acceleration of the user's head and for providing an output signal; and a processor for receiving the output signal and generating an event signal to trigger the intake or outflow of fluid by the telescoping member 116 by moving the outer circular member 117 to expose more or less of the perforated portions 119. In an embodiment, the acceleration threshold detector provides an output signal having a first value when the acceleration is less than a predetermined threshold and is arranged to switch the output signal from the first value to a second value when the acceleration reaches the predetermined threshold. The processor generates an event signal to trigger movement of the outer circular member 117 to expose more or less of the perforated portions 119, in response to the output signal from the acceleration threshold detector switching to the second value. In an embodiment, the acceleration threshold detector comprises at least one of a piezo element and a micromachined element. In an embodiment, the acceleration threshold detector is a Piezoresisitive 3-Axis acceleration sensor adapted to trigger an event (such as the intake or outflow or air by the telescoping member) when all outputs from X, Y or Z go below a predetermined set threshold. In an embodiment, the acceleration threshold detector is a MEMS accelerometer. A programmable sequence can control the movement of the outer circular member 117 to expose more or less of the perforated portions 119 such that at the predetermined threshold of acceleration there is a shut off of the fluid portal followed by a rapid release and then closure, repeating hundreds of times per second causing an oscillatory slowing of the acceleration to a full stop. If the head movement exceeds the set threshold then there is a rapid deceleration to return the movement to below threshold acceleration. Once set at a threshold, an accelerometer can activate the locking device in a lockable gas spring piston damper or the damping device in a dynamic gas spring piston damper. In an embodiment, the accelerometer may be set at a threshold of about 20 g or less or 3000 rads/second squared or less. Setting the accelerometer at this threshold may aid in preventing or ameliorating the chances of sustaining a concussion. In an embodiment, a pressure sensor integrator (rate of pressure increase and decrease) or air velocity measurement may be used in conjunction with the telescoping member 116 to set various thresholds to activate the locking device in a lockable gas spring piston damper or the damping device in a dynamic gas spring piston damper. In an embodiment, the device 110 may include an acceleration threshold detector with a set acceleration threshold and an electronic shut-off valve. In an embodiment, the acceleration threshold detector may be located on the front at a point between the eyes and mid forehead to detect acceleration in the coronal, sagittal and axial planes. When located vertically on the front, the acceleration threshold detector may detect acceleration on the sagittal plane. When located horizontally on the front, the acceleration threshold detector may detect acceleration on the axial plane. In an embodiment, the acceleration threshold detector may be located vertically at a point above the ear. This location may allow acceleration to be detected in the coronal plane.

The telescoping member 116 is sufficiently designed for extension and compression in a linear plane, and includes a first engaging member or connector 134 for engaging the first attachment member 132 of the headpiece 112, and a second engaging member or connector 137 for engaging an attachment member 136 of a support harness 138. In an embodiment, the connector 134 is a universal joint, allowing free movement in at least 180 degrees so that the telescoping member 116 remains linear. In an embodiment, the connector 134 and the first attachment member 132 attach to the strap 114a at the back of the head 113 at approximately the level of the inion. The inion represents the middle of the back of the head 113 and additionally is located equidistantly from bottom of skull to top. In an embodiment, the connector 134 of the telescoping member 116 can attach to a helmet at approximately the bottom base. The connector 134 may be detachable or removable from the first attachment member 132. The connector 134 may be fabricated from a joint, a hinge, a socket or any other device for coupling the headpiece 112 to the telescoping member 116 and allowing movement in more than one plane. In an embodiment, the connector 134 and the first attachment member 132 form a ball and socket joint allowing three degrees of freedom, permitting rotary movement in all directions through the movement of the connector 134 in the first attachment member 132. In such embodiments, the connector 134 terminates in a ball, and the first attachment member 132 terminates in a spherical shell sized to snugly envelope the ball of the connector 134. When the ball of the connector 134 is within the socket of the first attachment member 132, the centers of the ball and socket are coincident, resulting in a spherical geometry that facilitates full three dimensional rotation of the connector 134 and the first attachment member 132 about the coincident centers. In an embodiment, the ball and socket joint provides multi-axial and multi-directional positioning of the head. In an embodiment, the ball and socket joint allows free movement of the telescoping member 116 such that the telescoping member 116 remains in straight alignment and does not bend. In an embodiment, the connector 134 is made from a pliable material.

In an embodiment, the support harness 138 includes a vest or plate portion and straps sufficiently designed to secure to the user's torso. In an embodiment, the support harness may include a chest vest. In an embodiment, the support harness 138, designed as a vest, a plate or any other similar type device, is sufficiently designed to only secure to a user's torso and does not need to be secured to any other components such as, for example, components of a moving vehicle or sports training gear, to produce the desired protection. In an embodiment, the connector 37 attaches to the support harness 138 at the level of the C7/T1 spinous processes. The C7/T1 spinous processes represents the top or the torso and the base of the neck 115. In an embodiment, the support harness 138 includes a vest and/or a plate connecting a ball joint at approximately the level of the first thoracic spinous process. In an embodiment, the connector 137 can attach to a car seat in a vehicle that the user is in. The connector 137 may be detachable or removable from the second attachment member 136. The connector 137 may be fabricated from a joint, a hinge, a socket or any other device for coupling the support harness 138 to the telescoping member 116 and allowing movement in more than one plane. In an embodiment, the connector 137 and the second attachment member 136 form a ball and socket joint allowing three degrees of freedom, permitting rotary movement in all directions through the movement of the connector 137 in the second attachment member 136. In such embodiments, the connector 137 terminates in a ball, and the second attachment member 36 terminates in a spherical shell sized to snugly envelope the ball of the connector 137. When the ball of the connector 137 is within the socket of the second attachment member 136, the centers of the ball and socket are coincident, resulting in a spherical geometry that facilitates full three dimensional rotation of the connector 137 and the second attachment member 136 about the coincident centers. In an embodiment, the ball and socket joint provides multi-axial and multi-directional positioning of the head. In an embodiment, the ball and socket joint allows free movement of the telescoping member 116 such that the telescoping member 116 remains in straight alignment and does not bend. In an embodiment, the connector 137 is made from a pliable material.

Figure 11:
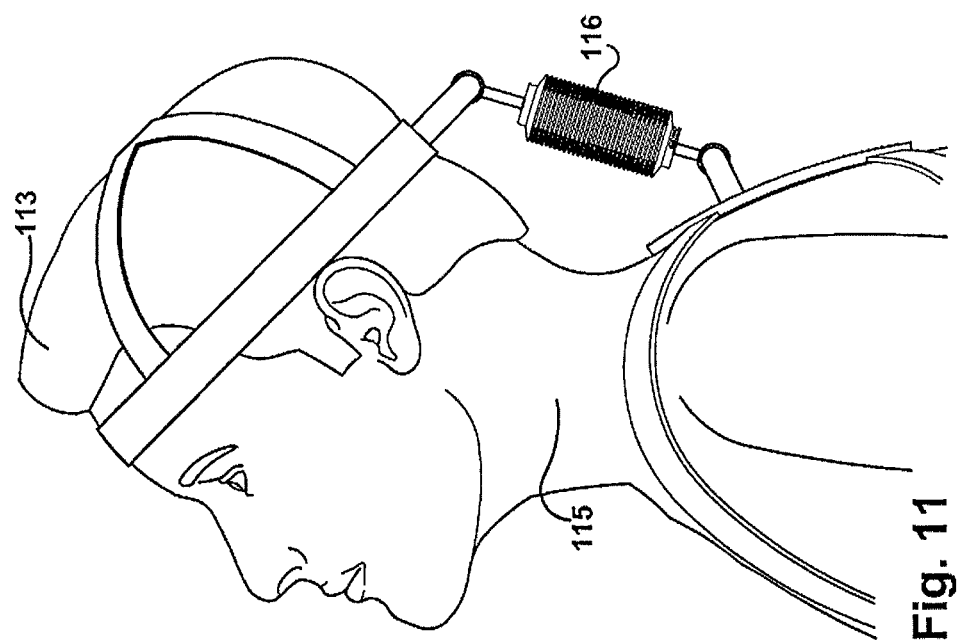
FIG. 11 shows a side view of the device of FIG. 9A on the user. The telescoping member is in a fully compressed state.

Similar to the telescoping member 28 of FIG. 2A, the accordion-like telescoping member 116 may compress the distance between the inion and first thoracic spinous process when the head 113 is fully extended, which is approximately two inches, and may extend the distance of about 8 inches between the inion and first thoracic spinous process when the head 113 is fully in flexion, which is approximately eight inches. In an embodiment, the accordion-like member 116 may include a collapsible and extendible tube. In an embodiment, the accordion-like member 116 may include a collapsible and extendible tube with a locking device. In an embodiment, the accordion-like member 116 may include an internal collapsible and extendible tube adapted to keep the accordion-like member 116 from bending. FIG. 11 shows the accordion-like telescoping member 116 in a fully compressed state where the head 113 and neck 115 are extended.

Figure 12:
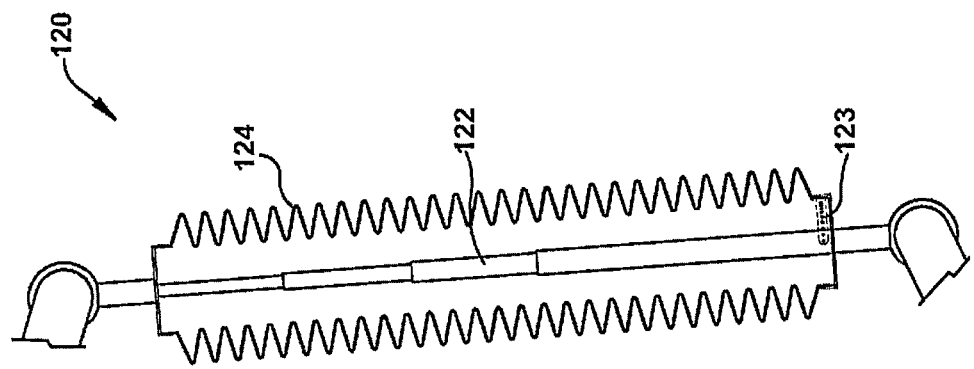
FIG. 12 shows a side view of an embodiment of a telescoping member of the present disclosure in a fully extended state.

FIG. 12 shows an embodiment of a telescoping member 120 of the present disclosure that can be used with a head harness and a support harness, as described above, to form a device of the present disclosure. The telescoping member 120 includes an inner telescoping member 122 situated inside of an outer accordion-like telescoping member 124. The inner telescoping member 122 acts to prevent bending of the outer accordion-like telescoping member 124 and to allow the outer accordion-like telescoping member 124 to remain in straight alignment with the headpiece of the device. In an embodiment, the outer accordion-like telescoping member 124 includes all or some of the features of the accordion-like telescoping member 116.

A device of the present disclosure can be used to prevent injuries that may occur, for example, during a vehicle crash, a sports accident, during battle and from a fall. Injuries that can be prevented include, but are not limited to, traumatic brain injury (TBI), cervical spine injuries, cervical spinal cord injuries, and cervical spine ligamentous injuries, among others. Symptomatic, non-penetrating brain injury, such as cervical spine and spinal cord injury, would be eliminated or markedly reduced with a device of the present disclosure. In an embodiment, a device of the present disclosure can reduce the incidence of brain, cervical spine, and spinal cord injury in crash victims, athletes, military and others while providing unencumbered head motion and range during normal circumstances.

TBI is a global health problem in terms of incidence, cost, and impact on daily living. Worldwide, an estimated 57 million individuals have been hospitalized with TBI. In the United States, medical center emergency rooms report approximately 1.74 million cases of mild TBI.

These estimates fail to include unrecognized or unreported TBI cases that may number up to 3 million for sports-related injuries and up to 40% for personnel participating in current military engagements. The type, direction, intensity, and duration of forces all contribute to the characteristics and severity TBI. Forces that may contribute to TBI include angular, rotational, shear, and translational forces A common pathway of injury is diffuse axonal injury (DAT), which is one of the most common and devastating types of TBI. DAI results from rotational shear forces that tear white matter tracts. Acceleration/deceleration TBI studies in animals and clinical investigations have attributed cognitive deficits to DAI. Distinguished from focal contusion without shearing, DAI is defined as damage to axons at the gray/white matter junction of the cerebral hemispheres, corpus callosum and dorsolateral midbrain and often involves the superior cerebellar peduncles. These deep white matter abnormalities can be detected by a MRI and are associated with poorer neuropsychological test performances and poor long-term outcome.

DAI disrupts attention and working memory networks by severing the connections in anterior white matter tracts that connect brain areas that carry out these functions and can also affect motor coordination. This disruption results in impaired timing on cognitive tasks, which is manifested as difficulty conversing, problem solving, regulating emotions and navigating daily activities-cognitive coordination problems. These difficulties can put those injured and others in immediate harm's way and lead to long term, persistent, unrecognized daily interaction problems. Similar to DAI, injuries to the cervical spine, ligaments and spinal accord occur mainly with rapid flexion and extension or torque of the neck.

The perforated portions of a telescoping member of the present disclosure may be variably exposed by the overriding rotatable circular member surrounding the outer diameter of the telescoping member. The outer circular member can expose more or less of the perforated portions as needed at the base of the telescoping member. In a situation where a user may experience a sudden impact which may ordinary (without use of a device of the present disclosure) lead to hyper-extension, hyper-flexion or hyper-angulation of the neck causing injury to the brain, cervical spine, and spinal cord, a user wearing a device of the present disclosure can reduce the incidence of hyper-extension, hyper-flexion or hyper-angulation of the neck preventing or substantially reducing injury to the brain, cervical spine, and spinal cord. In an embodiment, when the head and neck move from a neutral position to a flexed position (chin to chest direction) due to an injury, a telescoping member of the present disclosure is adapted to have a set threshold acceleration such that if the acceleration experienced by the user, which can be determined by an acceleration threshold detector in communication with the telescoping member or set by the number of perforated portions exposed at the base of the telescoping member, exceeds the set threshold acceleration, the telescoping member will stop extending initially, causing the head and neck to stop moving. This can immediately be followed by a release caused either by the fluid escaping under a lower acceleration through the set number of perforated portions or an electronically programmed series of releases guided by the acceleration threshold detector. In an embodiment, when the head and neck move from a neutral position to an extended position (head moves backward) due to an injury, a telescoping member of the present disclosure is adapted to have a set threshold acceleration such that if the acceleration experienced by the user, which can be determined by an acceleration threshold detector in communication with the telescoping member or set by the number of perforated portions exposed at the base of the telescoping member, exceeds the set threshold acceleration, the telescoping member will stop compressing initially, causing the head and neck to stop moving. This can be followed immediately by a release caused either by the fluid escaping under a lower acceleration through the set number of perforated portions or an electronically programmed series of releases guided by the acceleration threshold detector. In an embodiment, a device of the present disclosure prevents whip-lashing, thus preventing brain and cervical injury. In an embodiment, a device of the present disclosure protects the brain and cervical spine from a whiplash effect of the head in all directions (axes). The telescoping member of a device of the present disclosure remains in linear alignment due to the swiveling of the ball and socket joints.

In an embodiment, a device of the present disclosure stops movement immediately when acceleration or deceleration meets a certain set threshold which accordingly restricts the free flow of fluid. In an embodiment, an acceleration threshold detector adapted to determine the acceleration of a user's head provides an output signal to a processor and generates an event signal to indicate that the set threshold has been reached. In an embodiment, the number of perforated portions exposed at the base of the telescoping member sets the acceleration threshold. Following the immediate stop, the acceleration or deceleration drops below the set threshold allowing the free flow of fluid once again. In an embodiment, an acceleration threshold detector in tandem with a control mechanism of the rotatable circular member is programmed to analyze an input acceleration or deceleration and provide a signal to the control mechanism to expose or close a desired amount of the perforated portions. Movement may once again be restricted if the force which caused the initial acceleration or deceleration persists. In such a manner, a force applied to the head, such as in a blow to the head, will cause the head to move rapidly above a set threshold causing immediate restriction of movement but then releasing and restricting again as the head continues to be affected by the accelerating force. The net effect is a rapid stopping of movement followed by a series of stops and goes determined by the net accelerating/decelerating force and the number of perforated portions exposed or the accelerometer programming. In such a manner, the head and neck do not come to a sudden and complete stop, but rather a stop followed immediately by a rapid series of short releases and stops which will bring the head slowly to a halt. This dampening of the movement following the stop ensures that the brain and cervical spine never come to a rapid final stop causing strain in the neural tissues and surrounding supporting structures, but rather a stop followed by release and then dampening the reduction of movement over time.

A method for preventing brain and cervical spine injury includes positioning a device on a user, the device including a headpiece sufficiently designed to secure to a head of the user, the headpiece having an attachment member; a support harness sufficiently designed to secure to a torso of the user, the support harness having an attachment member; and a telescoping member sufficiently designed for extension and compression in a linear plane, the telescoping member having a first engaging member for engaging the attachment member of the headpiece, and a second engaging member for engaging the attachment member of the support harness; and setting a fixed acceleration threshold for the device, the fixed acceleration threshold representing a maximum acceleration for free movement of the user's head.

A person wearing a device of the present disclosure will have voluntary free head movement with respect to the torso. This voluntary movement is achieved by the telescoping member extending and compressing with minimal resistance when the head moves in any direction including the coronal, sagittal, and axial planes. The connector at each end of the telescoping member ensures that the member extends and compresses in a linear plane without bending.

In an embodiment, an inner airtight membrane of a telescoping member of the present disclosure fills with fluid on extension and exhausts fluid when the telescoping member compresses. The perforated portions of a telescoping member of the present disclosure are adapted to be in fluid communication with an opening in the airtight membrane allowing fluid to enter and exit the interior of the airtight membrane. The net surface area for fluid entry and exit may allow fluid movement easily at voluntary head movement speeds. Although the perforated portions are shown positioned at the base of the telescoping member, other locations for openings may be possible.

When a person wearing a device of the present disclosure is subjected to an external force such as a direct impact with resultant high acceleration or rapid deceleration such as in a car crash, the device may reduce the movement in a pattern that will decrease the brain tissue strain. Since a significant part of traumatic brain injury is the strain and resultant tearing of brain tissue from rapid acceleration or deceleration, a reduction in this strain force may lessen brain damage. A telescoping member of a device of the present disclosure will respond to rapid movement by extending or compressing, depending on the direction of the external force. The rapidity of the extension or compression will be limited by the rapidity of fluid intake (extension of the member) or rapidity of fluid exhaust (compression of the member) into and out of the airtight membrane, respectively. Therefore, the resistance to above normal head movement is by the extension or compression of the telescoping member determined by the resistance of fluid intake and fluid exhaust into and out of the interior of the airtight membrane.

The threshold for reducing above normal head movement may be changed by adjusting the surface area for fluid entry and exit. In an embodiment, a telescoping member of the present disclosure includes perforations that communicate with the interior of an airtight membrane. The surface area of the perforations can be increased or decreased by having an outer sliding or rotating circular member that can variable expose more or less perforations. When the rotating circular member is completely turned no perforations are exposed and the airtight membrane will not have fluid entry or exit and the telescoping member will not be able to extend or compress at all leading to no movement of the head. As the rotating circular member turns, revealing more perforations the threshold for resistance to rapid movement decreases allowing head movement. The person will be able to adjust the surface area of perforations to set a preferred threshold level.

A method for preventing brain and cervical spine injury includes providing a device comprising a headpiece sufficiently designed to secure to the user's head, the headpiece having a first attachment member; a support harness sufficiently designed to secure to the user's torso, the support harness having a second attachment member; an acceleration threshold device sufficiently designed to detect external forces experienced by the user's head and for providing an output signal to a processor circuit; and a telescoping member adapted to extend and compress in a linear plane by the intake and outflow of fluid, wherein the telescoping member has a first engaging member for engaging the first attachment member, the first engaging member and the first attachment member forming a ball and socket joint adapted to allow three degrees of freedom, permitting rotary movement in all directions through the movement of the first engaging member in the first attachment member, and wherein the telescoping member has a second engaging member for engaging the second attachment member, the second engaging member and the second attachment member forming a ball and socket joint adapted to allow three degrees of freedom, permitting rotary movement in all directions through the movement of the second engaging member in the second attachment member; connecting the first engaging member of the telescoping member with the first attachment member of the headpiece approximately at a level of the user's inion; connecting the second engaging member of the telescoping member with the second attachment member of the support harness approximately at a level of the user's C7/T1 spinous processes; detecting, using an acceleration threshold detector, external contact forces experienced by the user's head to determine acceleration of the user's head; providing, using the acceleration threshold detector, an output signal representing if the determined acceleration experienced by the user's head reached a predetermined threshold; receiving, using a processor, the output signal from the acceleration threshold detector; and generating, using the processor, an event signal to trigger the intake or outflow of fluid by the telescoping member in response to the determined acceleration. In an embodiment, the telescoping member has a main tube and a series of progressively smaller diameter tubes nested within each other. In an embodiment, the telescoping member has expansion bellows. In an embodiment, the telescoping member includes perforated portions allowing entrance and exit of fluid to and from the telescoping member during extension and compression of the telescoping member. In an embodiment, the fluid is a gas. In an embodiment, the fluid is a liquid. In an embodiment, an airtight membrane in fluid communication with the perforated portions covers an inside surface of the telescoping member and is adapted to house the fluid. In an embodiment, a rotatable circular member circumferentially surrounds an outer diameter of the telescoping member and is adapted to control the entrance and exit of fluid through the perforated portions. In an embodiment, the rotatable circular member is controlled by an accelerometer with a set threshold and a programmable sequence.

Measuring and recording the motion of human appendages and joints is a challenging problem. Results obtained from measuring and recording the motion of human appendages and joints have applications in medicine, sports, film, and video games. Furthermore, measuring the motion of the neck, or of the head relative to the torso, generates valuable data to evaluate and prevent brain and neck injuries. Medical and safety research has demonstrated that the motion of the neck plays an important role in the occurrence and severity of brain injury. However, there has been little advancement in the technology used to measure head and neck motion due to reliance on imprecise inertial measurement units, rigid or awkward attached devices, camera-based measurements, and test dummies with poor biofidelity.

Some mechanisms for measuring and recording the motion of human appendages and joints track targets attached to the subject using video cameras. These systems generally require specialize clothing, a fixed "stage" limited to the cameras' field of view, and a clear line-of-sight between the subject and the camera, etc. For instance, some systems use light emitters on multiple fiducials and a camera array to detect the light emitters and determining their positions in the same three-dimensional space. Measurements of this sort are limited by the camera's field of vision angle, are subject to depth perception limitations, and often times require filtering out ambient light, etc. When multiple cameras are used, calculations for merging the data collected quickly become complex and time consuming.

Other mechanisms utilize motion detection and distance sensors which have a relativistic component; they aim to locate an object of interest in free space as opposed to relative to a second object of interest. Utilizing these mechanisms to measure relative movement between limbs of a subject consequently requires unnecessary measurement and calculations of the movement of the subject's limbs in free space.

Some mechanisms used in the field of medicine, include devices for locating the tip of a probe or device within the body of a patient. For instance, a component may be used that is able to determine the relative separation between a probe and an instrument, or the relative position of a probe on a computerized image of the patient. Additionally, some devices measure a specific measurement of one dimension such as an angle between two vertebrae. Similarly, transmitters and receivers may be attached to the skin of a patient and the separation between the two may be measured. These specialized mechanisms are limited in their field of use, and cannot be used, or easily converted for use in measuring relational motion of a subject's limbs.

The aforementioned limitations are addressed by a subject-mounted relational motion detection system that is capable of measuring motion of a subject in order to determine the positions, velocities, and accelerations of at least two parts of the subject's body relative to one another. The subject-mounted relational motion detection system is used to measure the relative motion of physiological landmarks or fiducials, allowing the measurement and recording of the motion experienced by the subject. In some embodiments, the subject-mounted relational motion detection system is used to measure the relational position, velocity, and acceleration of body parts separated by flexible joints. Specifically, in some embodiments, the measurement of a subject's head relative to the subject's torso is accomplished by utilizing the subject-mounted relational motion detection system, which has the potential for improved tracking and measurement accuracy of relative motion.

In some embodiments, a subject-mounted relational motion detection system is provided. In some embodiments, the subject-mounted relational motion detection system is configured to track and measure the relative position, motion (direction and rotation), velocity, and/or acceleration of a subject's head relative to the subject's torso or vice versa. In other embodiments, similar systems are used to measure the relative position, velocity, and acceleration other of appendages, limbs, and/or joints. In some embodiments, the relational motion detection system tracks and measures the motion with up to six degrees of freedom.

Figure 13:
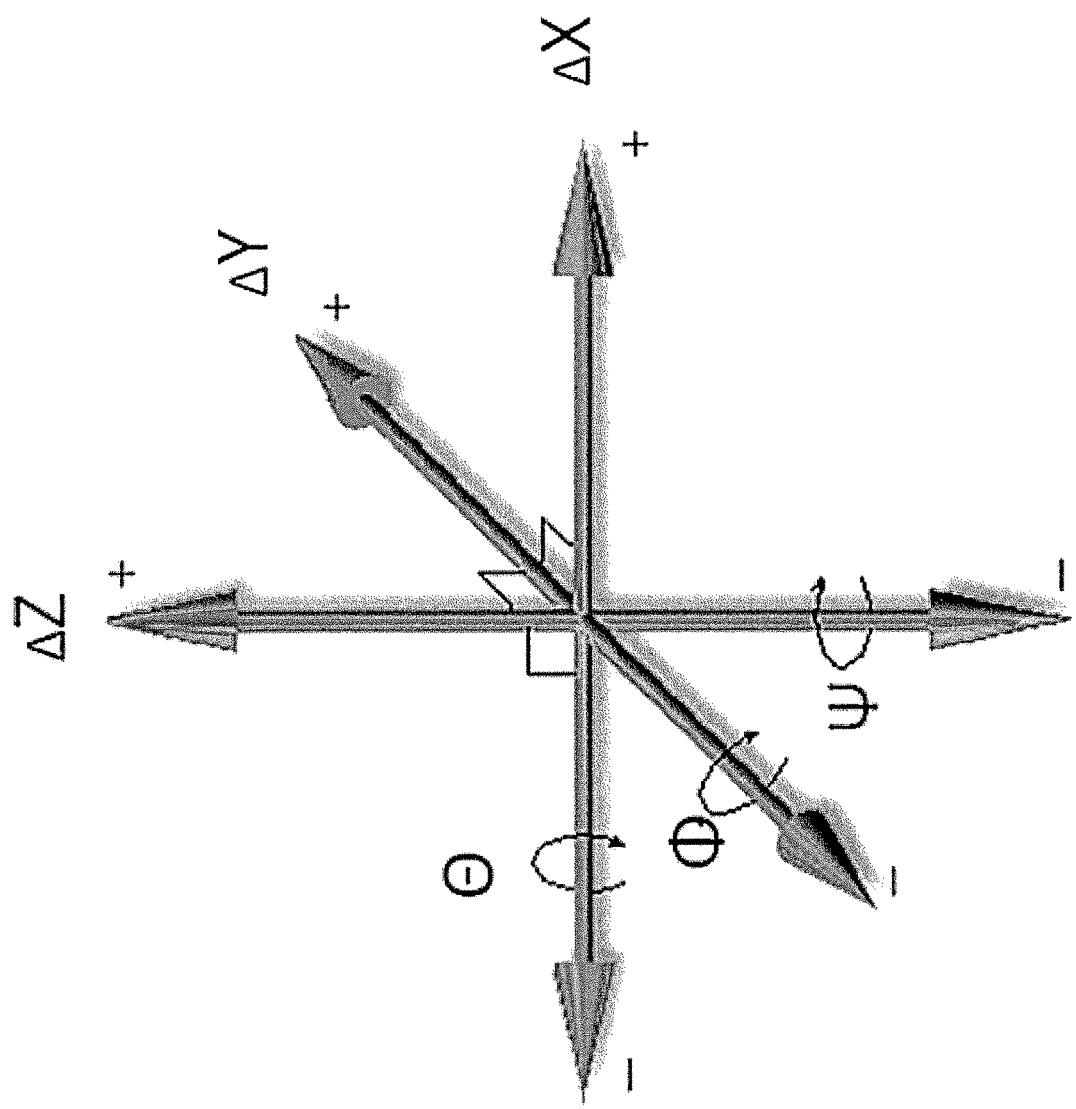
FIG. 13 shows the axes used for describing the relational motion of the subjects head with respect to their torso.

FIG. 13 shows the axes and rotations used for describing relational motion up to 6 degrees of freedom. As shown in FIG. 13, the axes of measurement include translation in three dimensions axial, coronal, and sagittal ($\Delta X$, $\Delta Y$ $\Delta Z$) as well as relative orientation pitch, yaw, roll ($\Phi$, $\Theta$, $\Psi$). The data from these measurements is used to monitor the usage, range of motion, or injury-related criteria. The data are measured for both the motion of a subjects head and the motion of the subject's torso. Then, the motion of the head relative to the torso of the subject is calculated. In some embodiments, this data is used to activate a therapeutic or protective device. In some embodiments, the data is communicated to external computers systems or personnel, either in real time or at the conclusion of a monitoring session. The communicated data is utilized for monitoring the relative motion of the head of the subject relative to the torso of the subject for therapeutic and research purposes.

Figure 14:
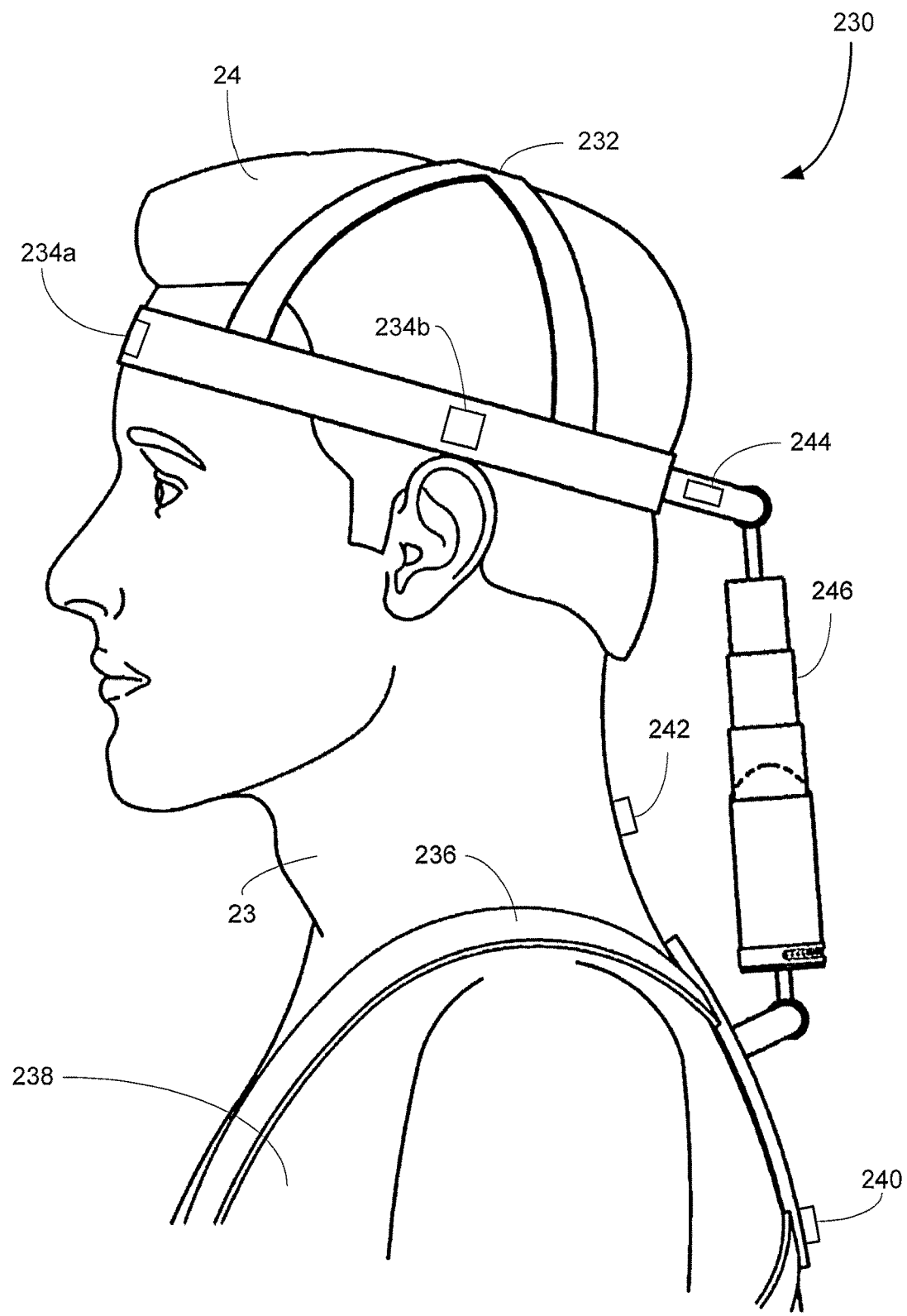
FIG. 14 shows a side view of an embodiment of a relational motion detection system of the present disclosure in a neutral position on a subject.

FIG. 14 illustrates a relational motion detection system 230 in accordance with some embodiments. The relational motion detection system 230 comprises a first apparatus 232 configured to be secured to a head 24 of a subject. In some embodiments, the first apparatus 232 includes the same elements as the headpiece 22 described in detail with respect to FIG. 2A. For instance, in some embodiments, the first apparatus 232 is composed of interconnected straps made out of leather, plastic, cloth, rubber, or the like. In other embodiments, the first apparatus 232 has a different configuration such as a hat, helmet, headband, chinstrap, or the like configured to be secured to a head 24 of a subject.

The first apparatus 232 includes at least a first motion detection sensor 234. The first motion detection sensor 234 is configured to measure a first motion—the motion of the head 24 of the subject. It is noted that in some other embodiments, the first motion detection sensor(s) 234 are attached directly to the subject's head without also being attached to the first apparatus 232. In other words, in some embodiments the first apparatus 232 is not used at all, or alternatively is not used to secure the first motion detection sensor(s) 234 to the subject's head 24, although it may still be used to dampen motion of the subject's head based on the measurements of the motion detection sensors as described in more detail below.

In some embodiments, the first apparatus 232 is configured to attach the first motion detection sensor 234 to the head 24 of the subject approximately between the subject's eyes and mid forehead, illustrated as a front located motion detection sensor 234a in FIG. 14. In other embodiments the front located motion detection sensor 234a is attached directly to the subject's head at the same position, without the use of the first apparatus 232. The front located motion detection sensor 234a, is mounted horizontally or vertically with respect to the subject's forehead. In some embodiments, when mounted vertically, the front located motion detection sensor 234a detects motion on the sagittal plane. In some embodiments, when mounted horizontally, the front located motion detection sensor 234a detects motion on the axial plane. Some embodiments include at least two front located motion detection sensors 234a, namely a vertical and a horizontal front located motion detection sensor 234a. These sensors detect motion in both the sagittal plane and the axial plane. In other embodiments, a single front located motion detection sensor 234a is configured to measure motion in both the sagittal plane and the axial plane.

In other embodiments, the first apparatus 232 is configured to attach the first motion detection sensor 234 to the head 24 of the subject approximately at a point vertically above the subject's ear, illustrated as a side located motion detection sensor 234b in FIG. 14. This location allows the side located motion detection sensor 234b to detect motion in the coronal plane. As mentioned above, in some embodiments the side located motion detection sensor 234b is attached directly to the subject's head at the same position without the use of any straps or the like.

The relational motion detection system 230 further comprises a second apparatus 236 configured to be secured to a torso 238 of a subject. In some embodiments, the second apparatus 236 includes the same elements as the support harness 38 described in detail with respect to FIG. 2A. For instance, in some embodiments, the second apparatus 236 is composed of a plate portion 40 and straps 41 sufficiently designed to secure to the user's torso. In other embodiments, the second apparatus 236 has a different configuration such as a vest, a shirt, bra, or the like configured to be secured to a torso 238 of a subject.

The second apparatus 236 includes at least a second motion detection sensor 240. The second motion detection sensor 240 is configured to measure a second motion—the motion of the torso 238 of the subject. It is noted that in some other embodiments, the second motion detection sensor(s) 240 are attached directly to the subject's torso the use of any straps or the like. For instance, it may be attached by adhesives.

In some embodiments, the second apparatus 236 includes a mechanism used to attach the second motion detection sensor 240 to the torso 238. In some embodiments the second motion detection sensor 240 is attached to the subject at approximately at high to mid thoracic level (T1 to T6) at the subject's midline. As described with respect to the first motion detection sensor(s) (234a and 234b), the second motion detection sensor(s) 240 may include vertically, horizontally, and obliquely mounted motion detection sensors 240, in order to detect motion in the sagittal plane, the axial plane, and the coronal plane. In other embodiments, a single motion detection sensor 240 is configured to measure motion in all three planes of movement.

It is noted that in alternative embodiments, the exact placement of the first motion detection sensor(s) 234 and the second motion detection sensor(s) 240 may differ from the placements described above. In these embodiments, first sensor(s) 234 and second sensor(s) 240 are positioned such that detection of movement in the sagittal, coronal, and axial planes is measured with respect to the referential position of the thoracic torso of the subject.

In some embodiments, the first motion detection sensor 234 and/or second motion detection sensor 240 is an accelerometer, gyroscope, magnetometer, or inertial measurement unit. In some embodiments, the first motion detection sensor 234 and/or second motion detection sensor 240 includes one or several of the following technologies to detect the relative positions of the head, neck, and torso:

Accelerometers, gyroscopes, and inertial measurement units

Flexible or rigid stretch and bend sensors

Laser, optical, RF/microwave, or ultrasonic, measurement of distances

Magnetic, resistive, inductive, or other proximity sensors

Digital image correlation using subject-mounted cameras

In some embodiments, one or more first motion detection sensor(s) 234 and/or second motion detection sensor(s) 240 may be used. Additionally, in some embodiments intermediate motion detection sensors attachments may optionally be made at points along the neck. Furthermore, additional (e.g., redundant) sensors may be used to improve accuracy and reliability. Additional and intermediate motion detection sensors are beneficial to obtain precise data and measure additional relative movements. Alternate embodiments with fewer motion detections sensors are beneficial in some instances to simplify implementation and/or reduce cost.

For instance, in some embodiments the relational motion detection system 230 optionally includes a third motion detection sensor 242, which is secured to the neck 23 of a subject. The third motion detection sensor 242 is configured to detect a third motion—the motion of the neck 23 of the subject. In some embodiments, the third motion detection sensor 242 is attached directly to the subject, as is illustrated in FIG. 14. In other embodiments, the third motion detection sensor 242 is secured to the subject's neck 23 using a third apparatus such as a collar, necklace, brace, or the like. As described with respect to the first motion detection sensor(s) 234, in some embodiments the third motion detection sensor(s) includes vertically, horizontally, and obliquely mounted motion detection sensors 242, mounted at the back and/or side of the subject's neck in order to detect motion in the sagittal plane, the axial plane, and the coronal plane. In other embodiments, a single motion detection sensor 242 is configured to measure motion in all three planes of movement.

The relational motion detection system 230 further comprises a control unit 244 configured to obtain information regarding the first motion from the first motion detection sensor 234 and the second motion from the second motion detection sensor 240. In some embodiments, the control unit 244 also obtains information third motion information from the third motion detection sensor 242. The control unit 244 is configured to obtain the motion information wired or wirelessly (e.g., through a Bluetooth connection) depending on the configuration of the relational motion detection system 230 and the sensors used. In some embodiments, the control unit 244 stores the obtained motion information. Furthermore, in some embodiments the control unit 244 is further configured to provide the motion information to an external device for calculation, persistent storage, and/or monitoring purposes.

In some embodiments, the control unit 244 contains instructions for calculating motion of the head 24 relative to the torso 238 of the subject based on the obtained first motion and second motion. Similarly, when the control unit is further configured to obtain third motion information from the third motion detection sensor 242, the control unit 244 contains instructions for calculating motion of the head 24 relative to the torso 238 of the subject based on the obtained first motion, second motion, and third motion. In some embodiments, the control unit 244 is further configured to provide the information regarding the calculated motion to an external device for monitoring the relative motion of the head of the subject relative to the torso of the subject and/or for persistent storage. In other embodiments, the control unit 244 is configured to provide instructions to dampen the movement of a subject's head 24 as described below.

In some embodiments, the relational motion detection system 230 further comprises a connector 246 such as the illustrated telescoping connector attached to the first apparatus 232 and the second apparatus 236. In some embodiments, the connector 246 includes the same elements as the telescoping member 28 described in detail with respect to FIG. 2A. For instance, in some embodiments, the connector 246 comprises a series of four tubes 42a, 42b, 42c and 42d of progressively smaller diameters nested within each other and may be made out of plastic, steel, metal, or any other light weight material to minimize bending of the member and allow for easy carrying. In other embodiments, the connector 246 includes the same elements as the telescoping member 116 described in detail with respect to FIG. 9A. For instance, in some embodiments, the connector 246 has accordion-like telescoping construction and includes expansion bellows 118 with convolutions that control the air which makes the telescoping connector 246 extend and compress. In still other embodiments the connector 246 utilizes a compressible material to dampen motion of the subject's head relative to the torso. As such, the connector 246 is configured to extend and compress freely during voluntary head movements and to extend and compress at reduced rates during high accelerations and rapid decelerations in order to dampen the subject's head and reduce the likelihood of injury.

In some embodiments, the telescoping connector 246 is configured to dampen motion of the subject's head 24 relative to the torso 238 of the subject. For instance, in some embodiments, the motion of the head 24 relative to the torso 238 of the subject is calculated by the control unit 244, and when the calculated motion exceeds a threshold the telescoping connector 246 dampens the motion of the subject's head 24 relative to the torso 238 of the subject. In some embodiments, this threshold is about 20 g or less or 3000 rads/second squared or less. This threshold may aid in preventing or ameliorating the chances of sustaining a concussion or other injury.

The telescoping connector 246 dampens motion of the subject's head 24 relative to the torso 238 of the subject using one or more of: hydraulic, pneumatic, and electromagnetic mechanisms. In some embodiments, the dampening is performed as described in detail with respect to FIGS. 2B and 9A. For instance, as explained in more detail with respect to FIG. 9A, when the calculated motion exceeds a threshold the control unit 244 generates an event signal to trigger movement of the outer circular member 117 (FIG. 9B) to expose more or less of the perforated portions 119. Similarly, when the calculated motion exceeds a threshold the control unit 244 generates an event signal to trigger movement of rotatable circular member 50, to expose perforated portions 46 (FIG. 2B). The outer circular member 50 can expose more or less of the perforated portions 46 as needed at the base of the telescoping member 28 (FIG. 2B).

It is noted that if the head 24 movement exceeds the set threshold then there is a rapid deceleration to return the movement to below the threshold acceleration. In some embodiments, the telescoping connector 246 will stop extending initially, causing the head and neck to stop moving. This can immediately be followed by a release caused either by the fluid escaping under a lower acceleration through the set number of perforated portions or an electronically programmed series of releases guided by the acceleration threshold detector. The telescoping connector 246 will stop compressing initially, causing the head and neck to stop moving, followed by an electronically programmed series of releases guided by the control unit 244. In other embodiments, the control unit maintains a more gradual deceleration using a feedback control system that constantly measures the relative motion of the sensors and adjusts the dampening accordingly. The feedback loop may be controlled by any suitable control scheme, such as a proportional-integral-derivative (PID) control scheme for dynamically dampening motion of the subject's head 24 relative to the torso 238 of the subject. As such, the presently described system prevents whip-lash or other brain or neck injuries.

The arrangement of the various components of the relational motion detection system 230 including but not limited to the first apparatus 232, the second apparatus 236, the telescoping connector 246, and the various motion detection sensors 234, 240, 242 are selected to maximize the number of degrees of freedom of motion that can be measured and/or controlled—namely, flexion/extension, lateral flexion, and torsion.

In some embodiments, the of the relational motion detection system 230 includes various additional components (not illustrated herein) including components for providing and maintaining power, for calibrating the system, for displaying settings and results, for data processing and recording, and for data communication.

Figure 15:
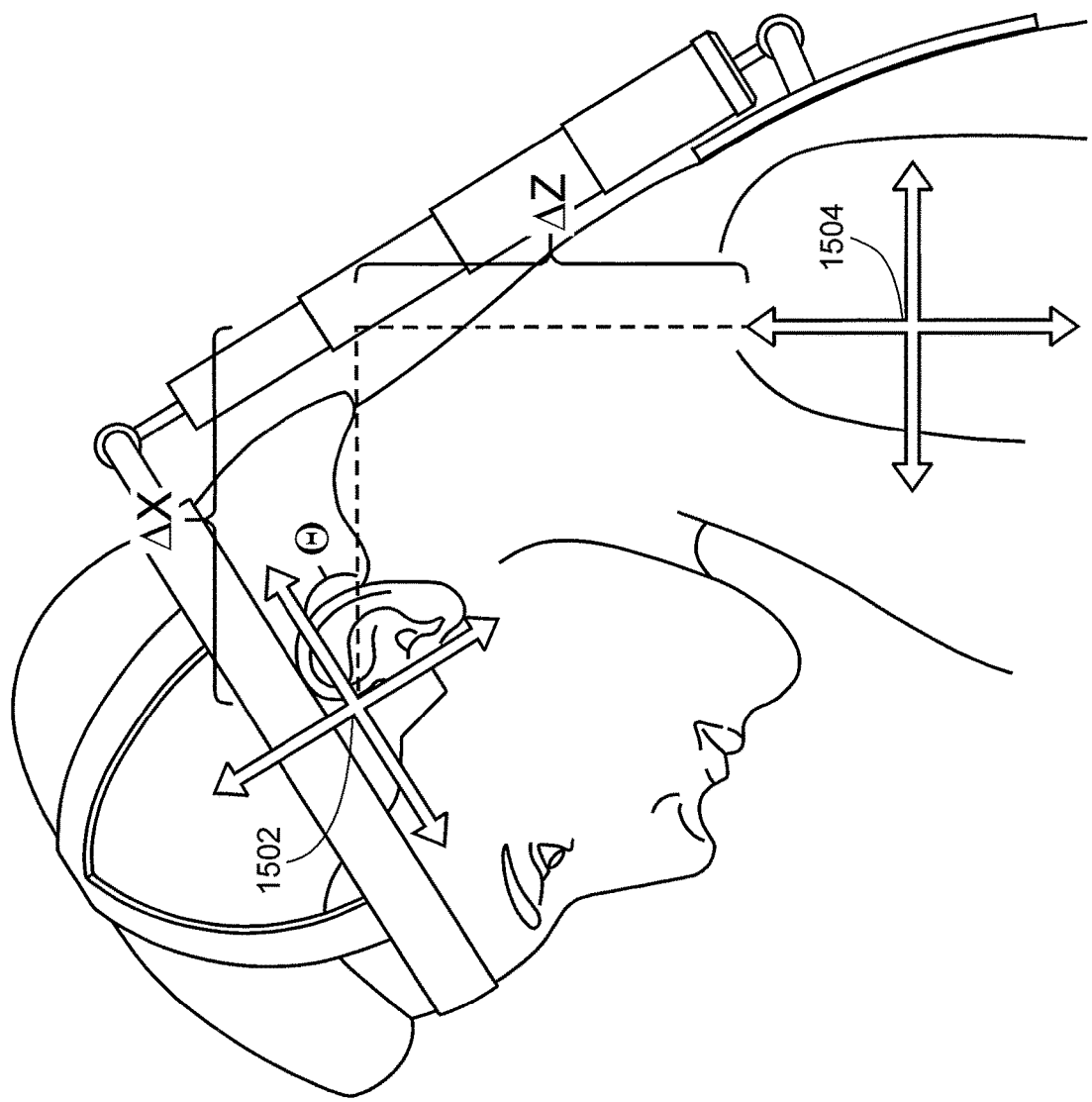
FIG. 15 shows a side view of an example of relational motion of a subject's head relative to the torso.

FIG. 15 shows a relational motion of a subject's head relative to the torso. The motion of the subject's head 1502 relative to the motion of the subject's torso 1504 is illustrated. This includes a motion in the sagittal plane, e.g., head snapping forward or a motion of nodding "yes," as shown. In this figure, the relational position and the orientation of the head is designated $\Delta X$ and $\Delta Z$, and the angle of rotation is designated $\Theta$.

Figure 16:
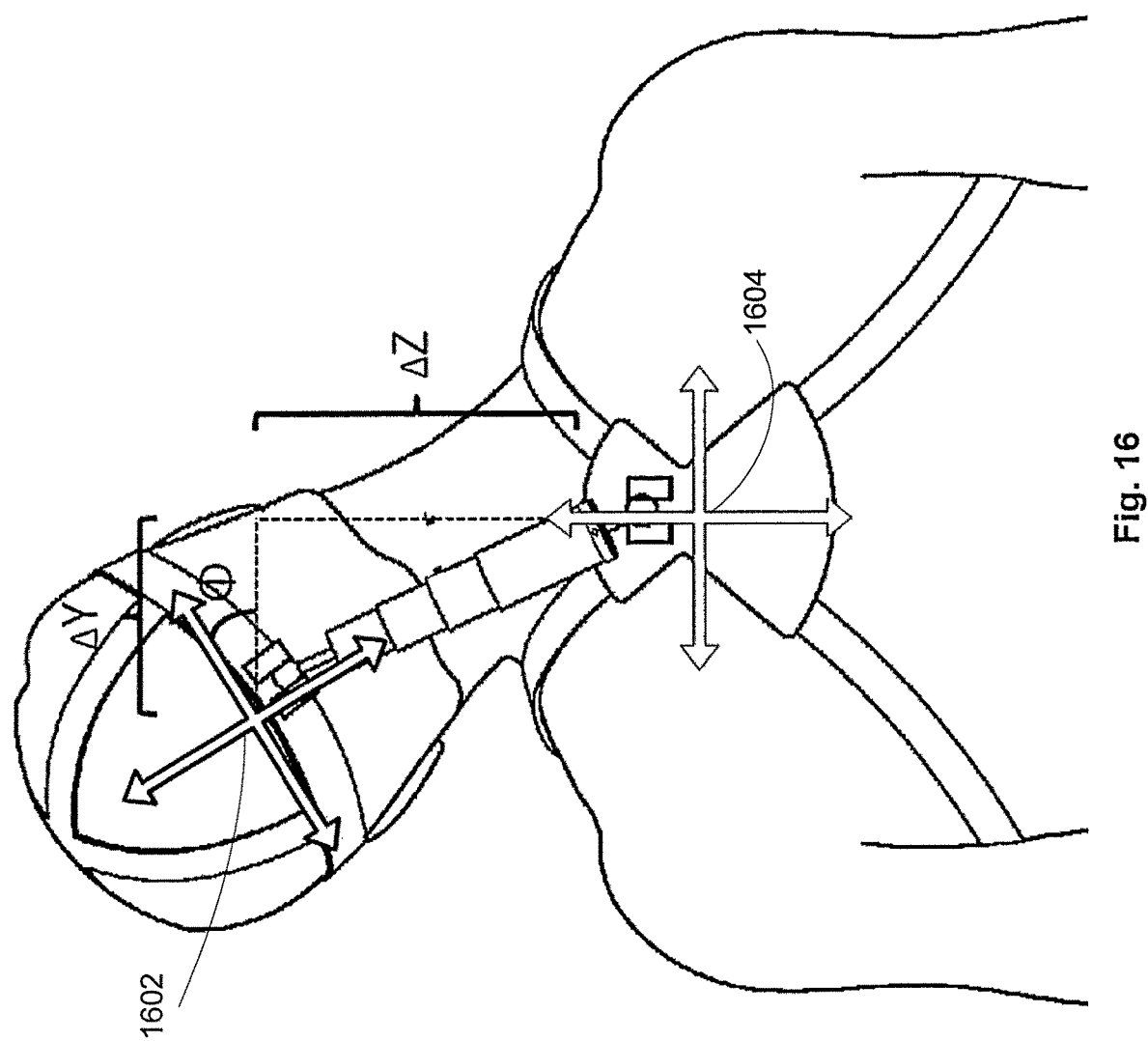
FIG. 16 shows a back view of an example of relational motion of a subject's head relative to the torso.

FIG. 16 also shows a relational motion of a subject's head relative to the torso. The motion of the subject's head 1602 relative to the motion of the subject's torso 1602 is illustrated. This includes a motion in the coronal plane, e.g., a head snapping sideways—ear toward the shoulder. In this figure, the relational position and orientation of the head is designated $\Delta Y$ and $\Delta Z$, and the angle of rotation is designated $\Phi$.

Figure 17:
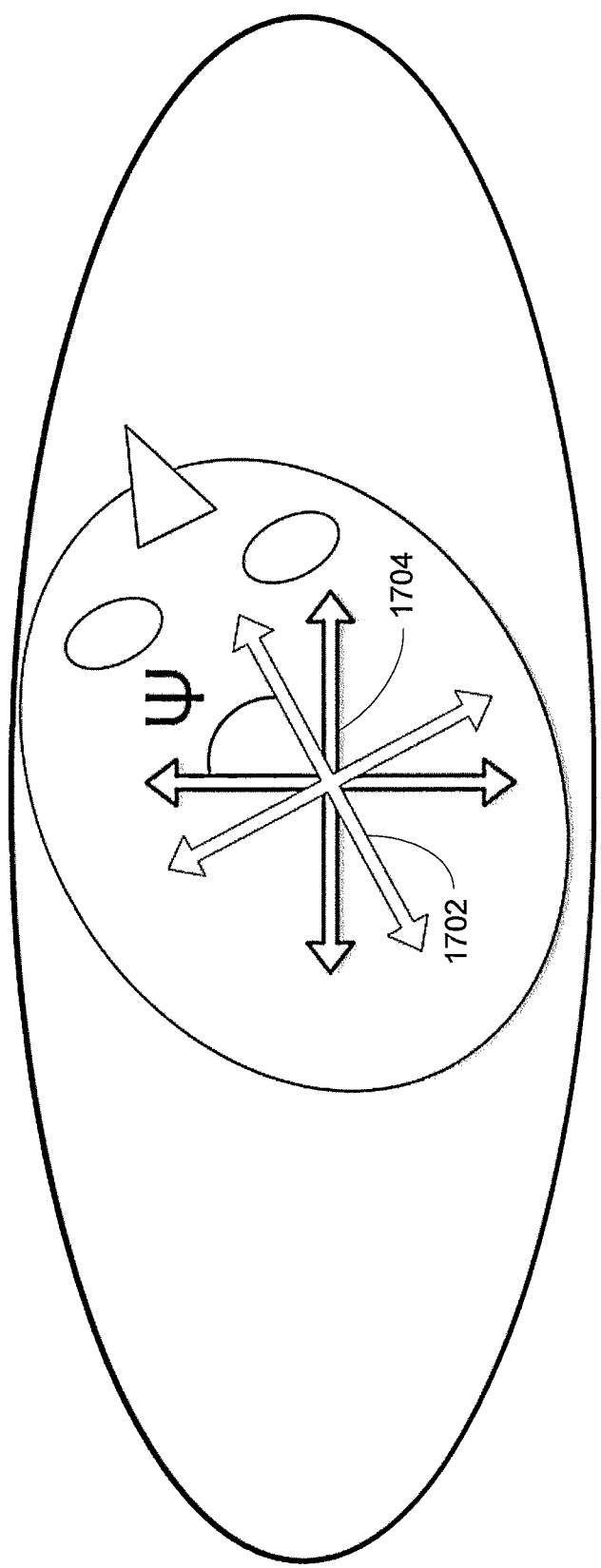
FIG. 17 shows a top view of an example of relational motion of a subject's head relative to the torso.

FIG. 17 shows yet another relational motion of a subject's head relative to the torso. The motion of the subject's head 1702 relative to the subject's torso 1704 is illustrated. This includes a rotational motion in the axial plane, e.g., a motion of shaking one's head "no." In this figure, the relational orientation of the head is designated W.

Figure 18:
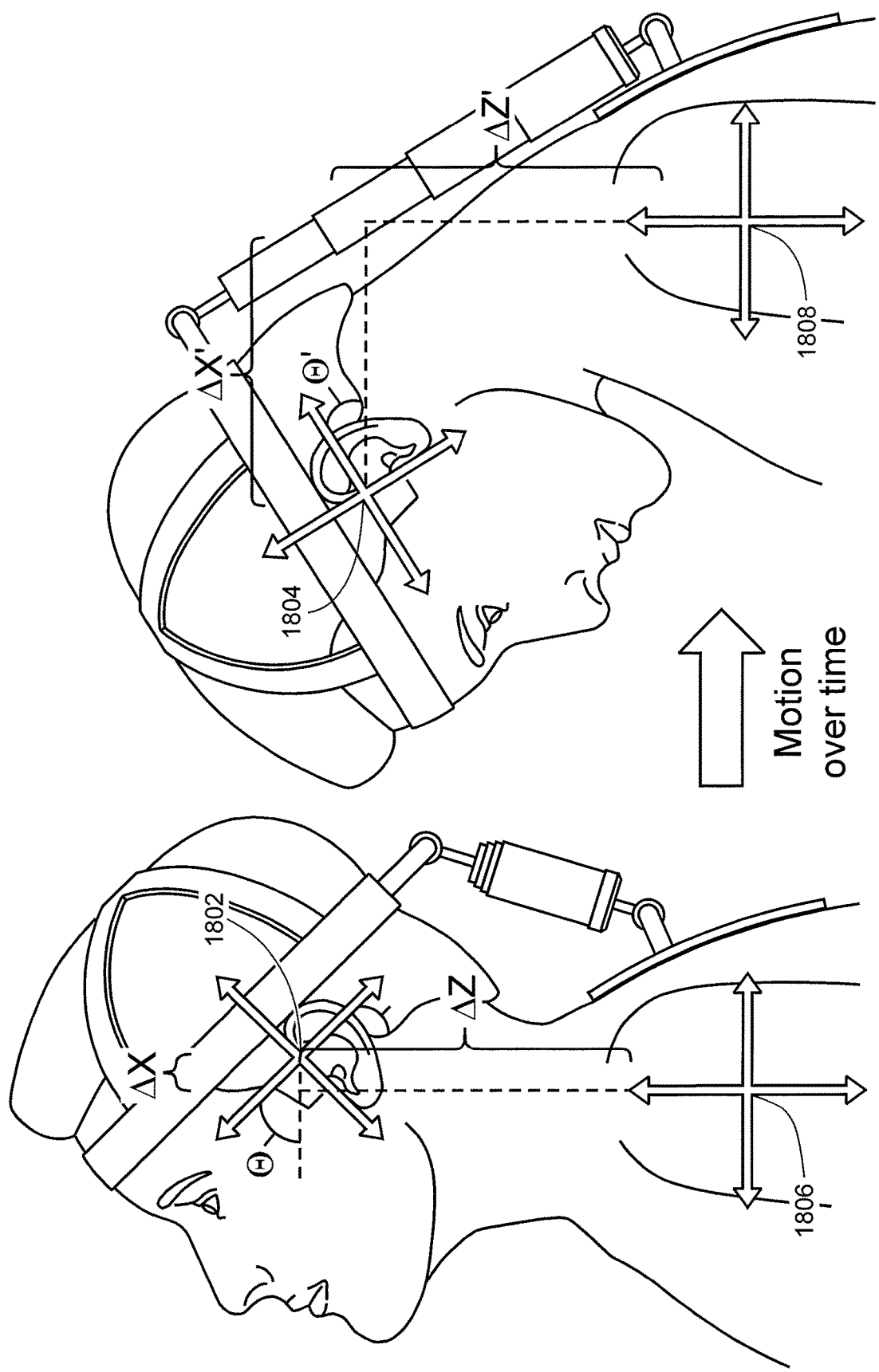
FIG. 18 shows a side view of an example of relational motion over time of a subject's head relative to the torso.

FIG. 18 shows a relational motion of a subject's head relative to the torso over time. Similar to FIG. 15, the motion illustrated is in the sagittal plane e.g., a motion of nodding "yes." The motion of the subject's head from a first position 1802 to a second position 1804 relative to the movement, if any, of the subject's torso from a first position 1806 to a second position 1808 is measured over an elapsed time (T'-T). The relational translational and angular velocity of the head is calculated by dividing the change in relational position ($\Delta X'$-$\Delta X$ and $\Delta Z'$-$\Delta Z$) and angle ($\Theta'$-$\Theta$), respectively, by the elapsed time (T'-T). As described below, in some embodiments, if the motion of the subject's head relative to the torso exceeds a threshold velocity or acceleration then the relational motion detection system dampens the subjects head motion to protect it from injury.

Figure 19:
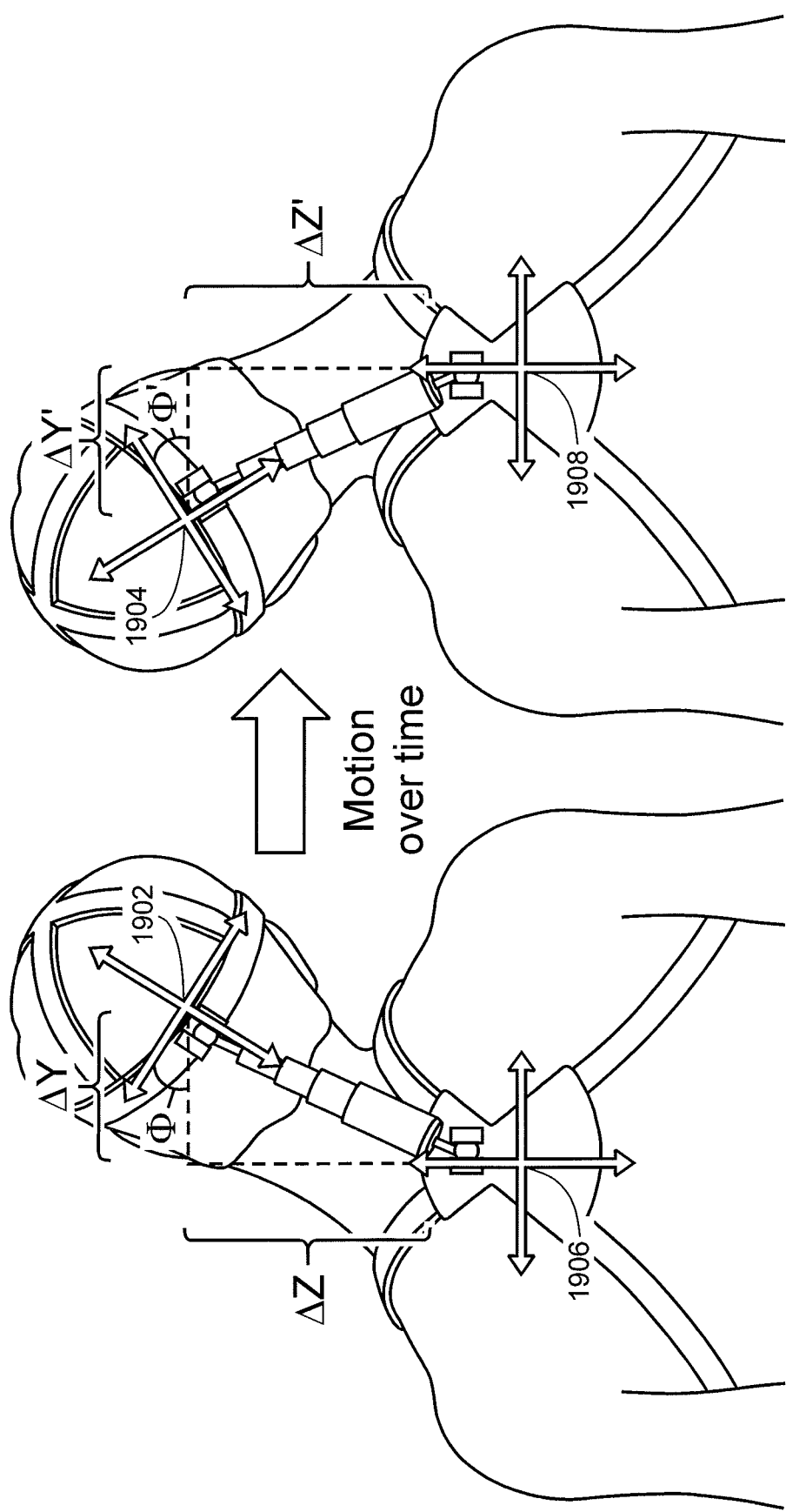
FIG. 19 shows a back view of an example of relational motion over time of a subject's head relative to the torso.

FIG. 19 shows another relational motion of a subject's head relative to the torso over time. Similar to FIG. 16, the motion illustrated is in the coronal plane, e.g., a motion of moving the ear toward the shoulder. The motion of the subject's head from a first position 1902 to a second position 1904 relative to the movement, if any, of the subject's torso from a first position 1906 to a second position 1908 is measured over elapsed time (T'-T). The relational translational and angular velocity of the head is calculated by dividing the change in relational position ($\Delta Y'$-$\Delta Y$ and $\Delta Z'$-$\Delta Z$) and angle ($\Phi'$-$\Phi$), respectively, by the elapsed time (T'-T).

Figure 20:
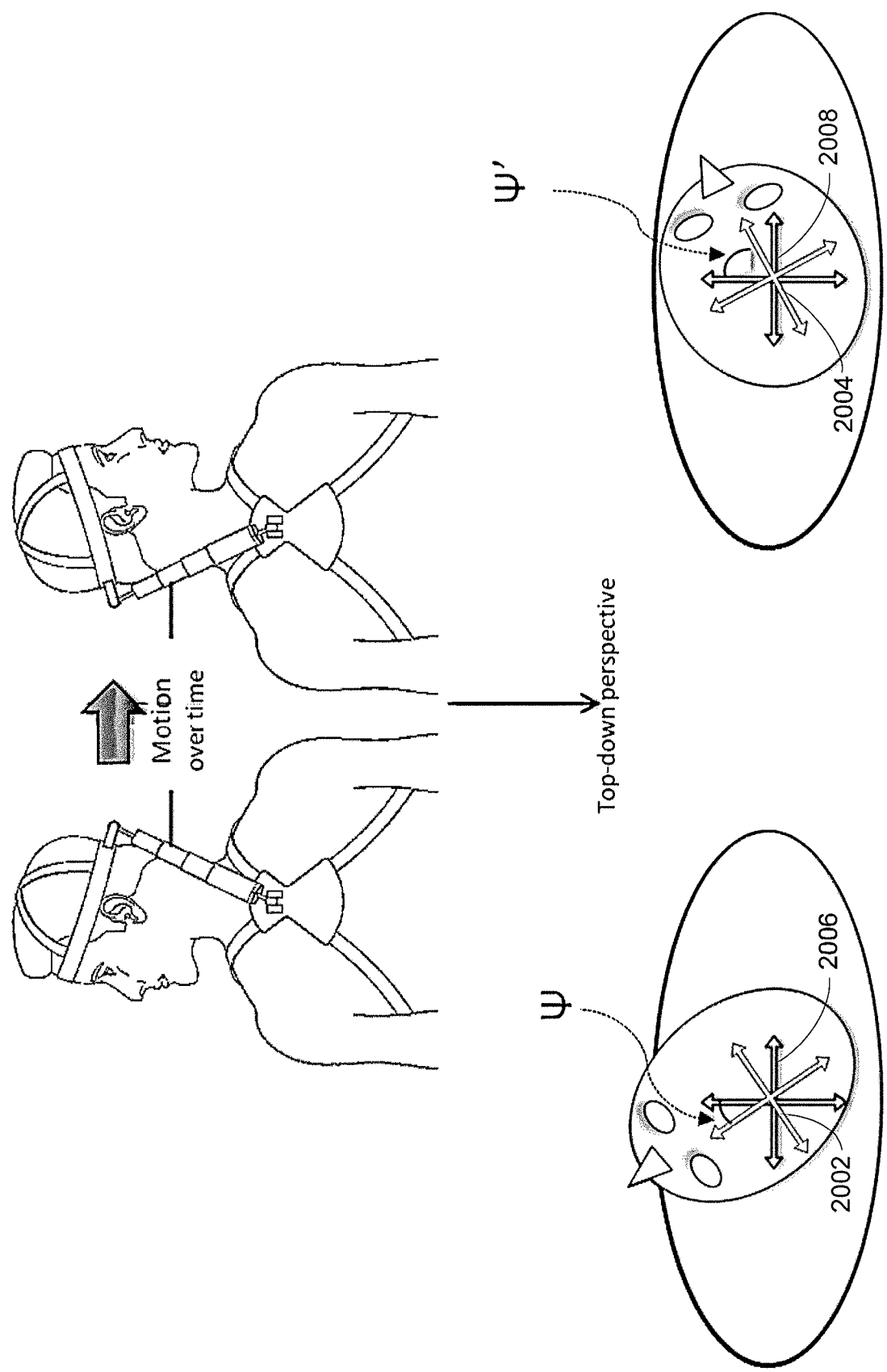
FIG. 20 shows other back and top views of an example of relational motion of a subject's head relative to the torso over time.

FIG. 20 shows yet a relational motion of a subject's head relative to the torso over time. Similar to FIG. 17, the illustrated rotational motion is in the axial plane, e.g., a motion of shaking one's head "no." The motion of the subject's head from a first position 2002 to a second position 2004 relative to the movement, if any, of the subject's torso from a first position 2006 to a second position 2008 is measured over elapsed time (T'-T). The relational angular velocity of the head is calculated by dividing the change in relational angle (e.g., $\Psi'$-$\Psi$) by the elapsed time (T'-T).

The relational detection system can detect and measure relative 3D movement of the head with respect to the torso, calculating specific spatial temporal patterns, which serve as thresholds for dampening. In some embodiments, the threshold is a relative acceleration in one plane, e.g., coronal. In some embodiments, the threshold is a pattern of movement over a short period of time in a twisting arc that has a combination of two or more of coronal, axial, and sagittal movement.

The relational motion detection system is capable of detecting a rapid acceleration the head with respect to the torso of a subject. Utilizing the collected information to dampen the head motion is advantageous in protecting a subject's head and neck from damage. The dampening can be used to prevent injuries that may occur, for example, during a vehicle crash, a sports accident, during battle and from a fall. Specifically, injuries that can be prevented include, but are not limited to, traumatic brain injury (TBI), cervical spine injuries, cervical spinal cord injuries, and cervical spine ligamentous injuries, among others. One of the most common and devastating types of TBI is diffuse axonal injury (DAI). DAI results from rotational shear forces that tear white matter tracts. Similar to DAI, injuries to the cervical spine, ligaments and spinal accord occur mainly with rapid flexion and extension or torque of the neck.

As such, in some embodiments an algorithm used to determine rapid flexion and extension of neck takes into account rapid movement of the head with respect to the torso in a combined coronal/axial plane.

In some embodiments, it is advantageous to prevent rapid rotation of the neck utilizing an algorithm that gives more weight to angular velocity/acceleration than to linear velocity/acceleration such as a whiplash motion of the head with acceleration in an upward or downward rotational motion.

In still other embodiments, it is useful to utilize an algorithm that combines and weighs the various components including integrated coronal, sagittal and axial rotations producing a spatial temporal map of relative head to torso movement.

In some embodiments, the dampening process is triggered at differing thresholds. The threshold is set by the user or supervisor (e.g., medical professional) to meet the subject's specific needs. For instance, race car drivers may have a lower threshold in all planes since the driver's has little head movement whereas football players may have a higher threshold in all planes due to need for rapid head movements.

As such, the relational motion detection system is used to prevent injuries by providing dampening for the subjects head when the motion of the subject's head relative to the torso triggers an appropriate threshold. Additionally the relational motion detection system provides unencumbered head motion and range during circumstances where the motion of the subject's head relative to the torso does not reach the threshold.

Figure 21A:
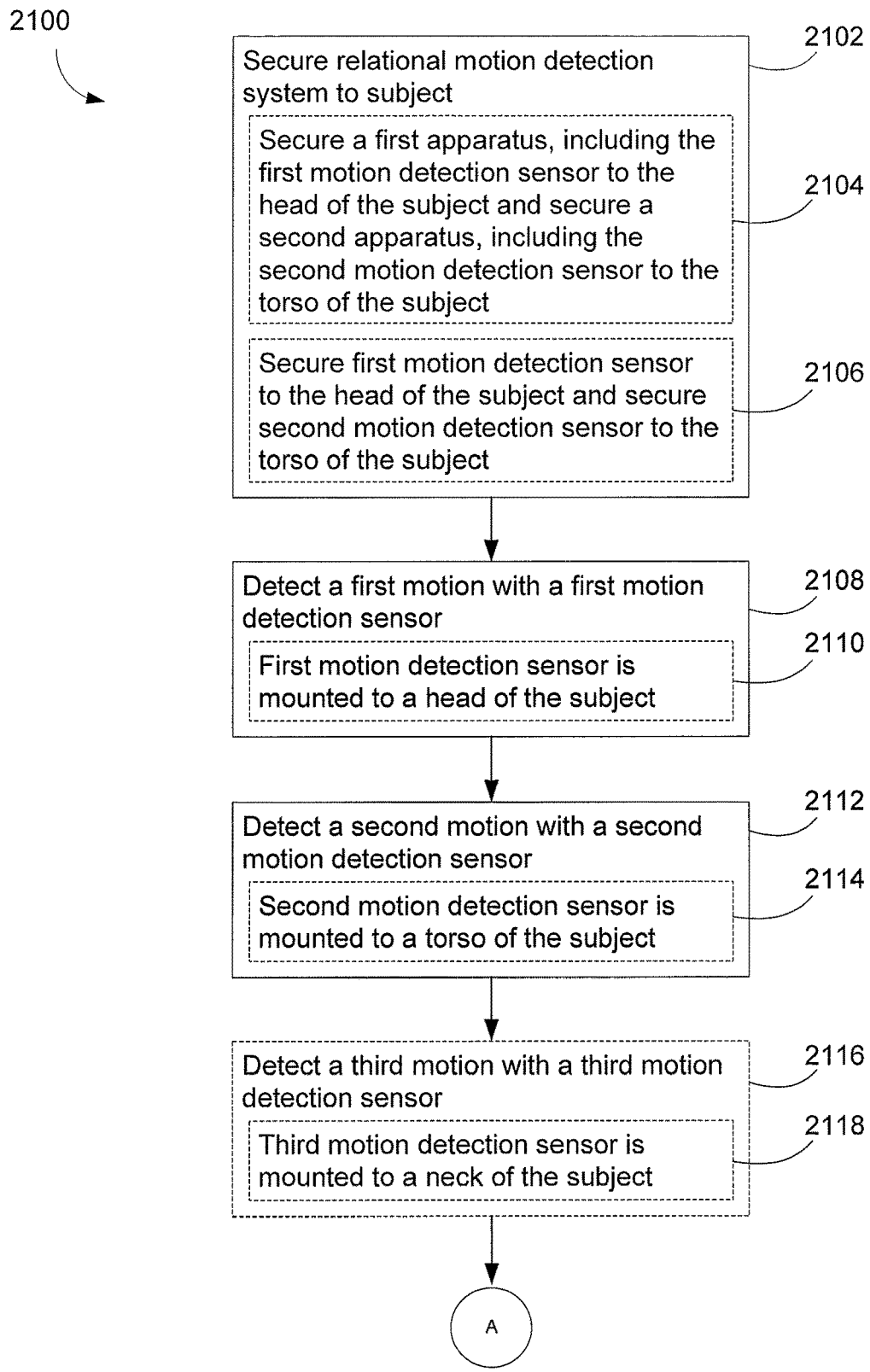
FIGS. 21A and 21B show a method for measuring relative motion of a head of a subject relative to a torso of a subject, as performed by the relational motion detection system.
Figure 21B:
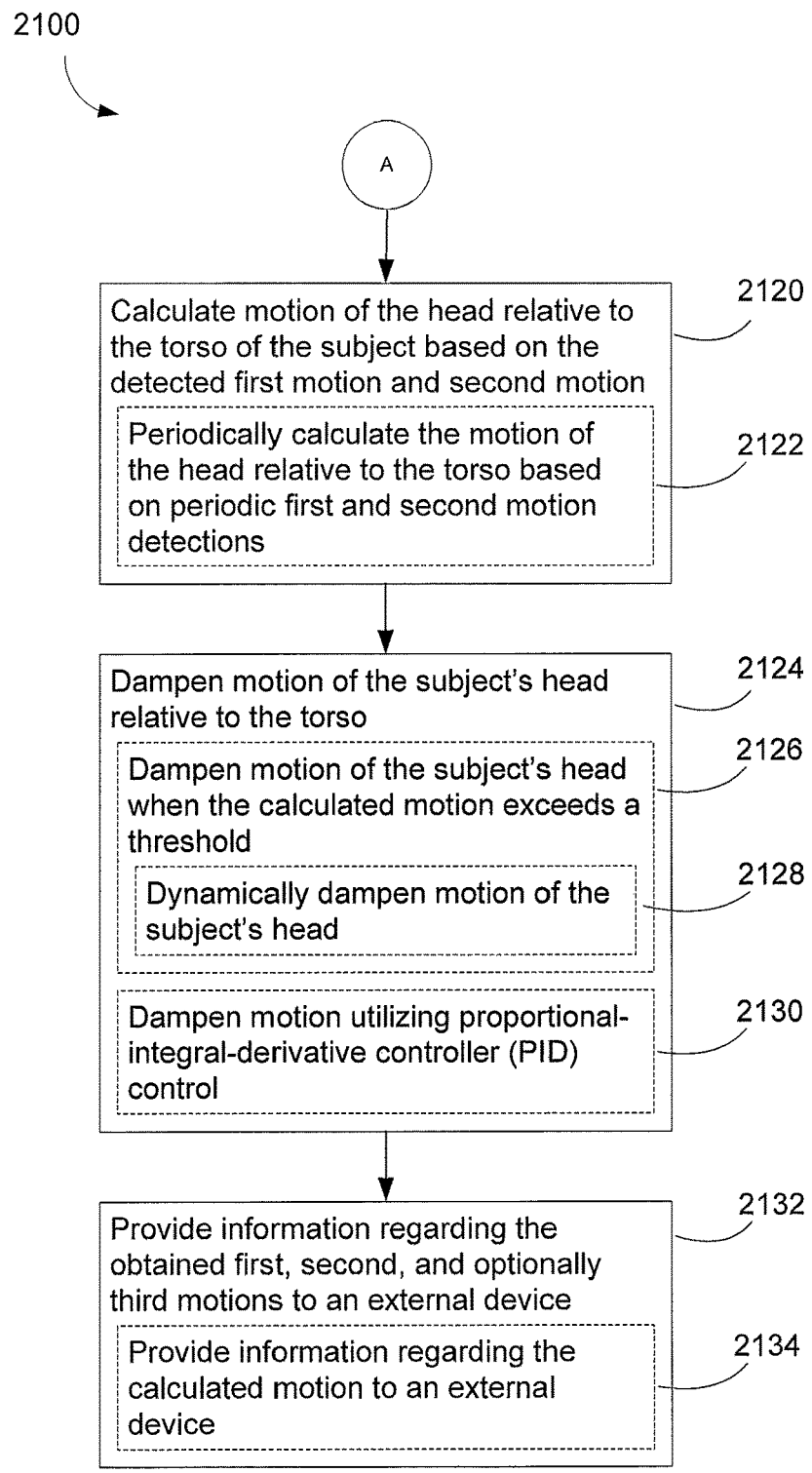

FIGS. 21A and 21B show a method 2100, performed by the relational motion detection system, for measuring relative motion of a head of a subject relative to a torso of a subject according to certain embodiments. The method is performed by various components of the relational motion detection system described with respect to FIG. 14.

In some embodiments, the method (2100) begins by securing the relational motion detection system to the subject (2102). For instance, a first apparatus, including the first motion detection sensor is secured to the head of the subject; and a second apparatus, including the second motion detection sensor is secured to the torso of the subject (2104). In some instances the securing includes attaching and tightening the first apparatus by tightening straps around the head of a subject. Similarly, the second apparatus is secured in some instances by donning a vest or tightening straps to attach it to the torso of the subject. It is noted that in some other embodiments, the first motion detection sensor is secured directly to the head of the subject and the second motion detection sensor is secured directly to the torso of the subject without being attached to the first or second apparatuses respectively (2106). As such, the first and second sensors are attached to using adhesive, straps, or other devices, or are attached to or integrated in other protective equipment, uniforms, or other garments comprising the first and second apparatuses of the subject mounted relational motion detection system.

In some embodiments, the method (2100) of measuring relative motion of a head of a subject relative to a torso of a subject begins with detecting a first motion with a first motion detection sensor (2108). First motion may include a motion along one or more of an axial plane, a coronal plane, and a sagittal plane and/or an angel of rotation. In preferred embodiments, first motion detection sensor is mounted to a head of a subject (2110).

The method (2100) continues by detecting a second motion with a second motion detection sensor (2112). Second motion may include a motion along one or more of an axial plane, a coronal plane, and a sagittal plane and/or one or more angles of rotation. In preferred embodiments, the second motion detection sensor is mounted to a torso of the subject (2114).

In some embodiments, detecting the first motion and the second motion includes measuring motion in an axial plane, a coronal plane, and/or a sagittal plane. In some embodiments, detecting the first motion and the second motion additionally or alternatively includes measuring at least one angle of rotation. As such, in some embodiments detecting the first motion and the second motion includes measuring up to all six degrees of freedom. Furthermore, the detected motion may also include a time component—such that acceleration or velocity in any of the aforementioned planes or angles of rotation is measured or calculated.

In optional embodiments, the method (2100) also includes detecting a third motion with a third motion detection sensor (2116). In some embodiments, the third motion detection sensor is mounted to a neck of the subject (2118). In other embodiments the third motion detection sensor is a redundant sensor used to more accurately calibrate or measure the motion of the subjects head or torso. For instance, in some embodiments sensors are mounted to both sides of the user's head above the ears in order to measure movement in the coronal plane. In still other embodiments the third sensor is mounted to a shoulder of the subject (or sensors are mounted on both of the subject's shoulders) in order to provide information about independent motion of the shoulder with respect to the subject's torso, and or head and torso combination movement. As discussed with respect to the first and second motions, detecting the third motion includes measuring motion in any or all of the aforementioned planes or angles of rotation. Furthermore, in some embodiments an acceleration or velocity of that motion is also measured or calculated.

In FIG. 21B the method (2100) continues with calculating motion of the head relative to the torso of the subject based on at least the detected first motion and second motion (2120). In embodiments that includes detecting a third motion, calculating motion of the head relative to the torso of the subject based on the detected first motion, second motion, and third motion. In some embodiments, the detecting the first motion (2108), detecting the second motion (2112), and when applicable detecting the third motion (2116), are all performed periodically. The measurements are taken at a first time T and then again at a second time T' as illustrated with respect to FIG. 18-FIG. 20. In some embodiments, they are then taken again such that the time elapsed is T' to T". The calculating of the motion of the head relative to the torso of the subject based on at least the detected first motion and second motion is thus also performed periodically (2122). Furthermore, in some embodiments continuous subsequent calculations are also performed such that the product is a three dimensional representation of the referential movement of the head with respect to the torso over time.

In some embodiments, the method (2100) further includes dampening motion of the subject's head relative to the torso of the subject (2124). For instance, the dampening is performed in some instances when the calculated motion exceeds a threshold (2126), as described with reference to FIG. 14. In embodiments where the motion of the head relative to the torso is periodically calculated, the method (2100) further comprises dynamically dampening motion of the subject's head relative to the torso of the subject when the periodically calculated motion exceeds a threshold. In some embodiments, the dynamically dampened motion is controlled using proportional-integral-derivative controller (PID) control (2130) as explained in more detail with respect to FIG. 14.

Finally, in some embodiments, the method (2100) also includes providing information regarding the first, second, and (optionally third) motions to an external device (2134). In some embodiments, the external device then performs the motion calculations of (2120) and (2122). In other embodiments, the motion of the head relative to the torso of the subject is calculated within the relational motion detection system, and the calculated motion is then provided to an external device (2134). In either embodiment, the information provided to the external device is used for monitoring or analysis of the motion of the head of the subject relative to the torso of the subject. This monitoring and analysis is useful for various applications such as diagnostics, therapeutics, and research. As it can be used to monitor usage of the limbs, range of motion, or injury criteria. For instance, the above described system and method of using the system is especially applicable for the monitoring of, detection of, and protection from traumatic brain injury.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

All patents, patent applications, and published references cited herein are hereby incorporated by reference in their entirety. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. An injury reduction system comprising:
   a first motion detection sensor on a first apparatus configured to be secured to a head of a subject to detect a first motion of the head of the subject;
   a second motion detection sensor on a second apparatus configured to be secured to a torso of the subject to detect a second motion of the torso of the subject;
   a telescoping connector, coupled to the first apparatus and the second apparatus, configured to dampen relative motion of the subject's head relative to the torso of the subject; and
   a control unit configured to obtain information regarding the first motion from the first motion detection sensor and the second motion from the second motion detection sensor;
   wherein the control unit contains instructions for:
      calculating a relative motion of the head relative to the torso of the subject by comparing the obtained first motion and second motion;
      determining whether the calculated relative motion of the head relative to the torso of the subject exceeds a predetermined threshold; and
      in response to determining that the calculated relative motion of the head relative to the torso of the subject exceeds the predetermined threshold, dampening the relative motion of the head relative to the torso of the subject using the telescoping connector.

2. The system of claim 1, wherein the control unit is further configured to provide the information regarding the calculated relative motion to an external device for monitoring the relative motion of the head of the subject relative to the torso of the subject.

3. The system of claim 1, further comprising:
   a third motion detection sensor to be secured to the neck of a subject to detect a third motion;
   wherein the control unit is further configured to obtain third motion information from the third motion detection sensor; and
   wherein the control unit contains instructions for calculating a relative motion of the head relative to the torso of the subject based on the obtained first motion, second motion, and third motion.

4. The system of claim 1, wherein said dampening comprises gradually decelerating the relative motion of the head relative to the torso of the subject by:
   recalculating the relative motion of the head relative to the torso of the subject; and
   adjusting the dampening of the relative motion of the head relative to the torso in accordance with said recalculating.

5. The system of claim 1, wherein the telescoping connector dampens relative motion of the subject's head relative to the torso of the subject using one or more of: hydraulic, pneumatic, and electromagnetic mechanisms.

6. The system of claim 5, wherein the control unit further comprises a proportional-integral-derivative (PID) controller for controlling said dampening.

7. The system of claim 1, wherein the telescoping connector dampens relative motion of the subject's head relative to the torso of the subject using a compressible material.

8. The system of claim 1, wherein the first apparatus is configured to attach the first motion detection sensor to the head of the subject approximately between the subject's eyes and mid forehead.

9. The system of claim 1, wherein the first apparatus is configured to attach the first motion detection sensor to the head of the subject approximately at a point vertically above the subject's ear.

10. The system of claim 1, wherein the second apparatus is configured to attach the second motion detection sensor to the torso of the subject at approximately high to mid thoracic level at the subject's midline.

11. The system of claim 1, wherein one or both of the first motion detection sensor and second motion detection sensor includes one or more of: an accelerometer, gyroscope, magnetometer, and inertial measurement unit.

12. A method of reducing injury from relative motion of a head of a subject relative to a torso of a subject, comprising:
   detecting a first motion of the head of the subject using a first motion detection sensor coupled to a first apparatus that is secured to the head of a subject;
   detecting a second motion of the torso of the subject using a second motion detection sensor coupled to a second apparatus that is secured to the torso of the subject;
   calculating a relative motion of the head relative to the torso of the subject by comparing the detected first motion and second motion;
   determining whether the calculated relative motion of the head relative to the torso of the subject exceeds a predetermined threshold; and
   in response to determining that the calculated relative motion of the head relative to the torso of the subject exceeds the predetermined threshold, dampening, via a telescoping connector coupled to the first apparatus and the second apparatus, the relative motion of the head relative to the torso of the subject.

13. The method of claim 12, wherein said dampening is controlled using a proportional-integral-derivative controller.

14. The method of claim 12,
   wherein the predetermined threshold is based on one or more of: a velocity, an acceleration, and a specific spatial temporal pattern.

15. The method of claim 12, wherein detecting the first motion, detecting the second motion, and calculating are performed periodically.

16. The method of claim 12, further comprising after the calculating:
   providing information regarding the calculated relative motion to an external device for monitoring of the motion of the head of the subject relative to the torso of the subject.

17. The method of claim 12, wherein said dampening comprises gradually decelerating the relative motion of the head relative to the torso of the subject by:
   recalculating the relative motion of the head relative to the torso of the subject; and
   adjusting the dampening of the relative motion of the head relative to the torso in accordance with said recalculating.

18. The method of claim 12, wherein detecting the first motion and the second motion further comprises measuring an acceleration or velocity.

19. The method of claim 12, wherein detecting the first motion and the second motion further comprises measuring at least one angle of rotation.

20. The method of claim 12, wherein detecting the first motion and the second motion further comprises measuring motion along one or more of an axial plane, a coronal plane, and a sagittal plane.

21. The method of claim 12, wherein detecting the first motion and the second motion further comprises measuring up to six degrees of freedom.

22. The method of claim 12, further comprising:
  detecting a third motion with a third motion detection sensor mounted to a neck of the subject; and
  calculating a relative motion of the head relative to the torso of the subject based on the detected first motion, second motion, and third motion.

* * * * *